US010568526B2

(12) United States Patent
McKenna et al.

(10) Patent No.: US 10,568,526 B2
(45) Date of Patent: Feb. 25, 2020

(54) COMBINED PHYSIOLOGICAL SENSOR SYSTEMS AND METHODS

(71) Applicant: Covidien LP, Mansfield, MA (US)

(72) Inventors: Edward M. McKenna, Boulder, CO (US); Bo Chen, Louisville, CO (US); Youzhi Li, Longmont, CO (US); Paul Stanley Addison, Edinburgh (GB)

(73) Assignee: Covidien LP, Mansfield, MA (US)

( * ) Notice: Subject to any disclaimer, the term of this patent is extended or adjusted under 35 U.S.C. 154(b) by 530 days.

(21) Appl. No.: 14/860,475

(22) Filed: Sep. 21, 2015

(65) Prior Publication Data

US 2016/0015281 A1  Jan. 21, 2016

Related U.S. Application Data

(63) Continuation of application No. 13/020,704, filed on Feb. 3, 2011, now Pat. No. 9,138,183.

(60) Provisional application No. 61/301,088, filed on Feb. 3, 2010.

(51) Int. Cl.
*G06F 15/00* (2006.01)
*G01N 33/48* (2006.01)
*A61B 5/0205* (2006.01)
*A61B 5/01* (2006.01)
*A61B 5/024* (2006.01)
*A61B 5/16* (2006.01)
*A61B 5/00* (2006.01)
*A61B 5/1455* (2006.01)

(52) U.S. Cl.
CPC ............ *A61B 5/02055* (2013.01); *A61B 5/01* (2013.01); *A61B 5/0205* (2013.01); *A61B 5/02433* (2013.01); *A61B 5/14552* (2013.01); *A61B 5/165* (2013.01); *A61B 5/6814* (2013.01); *A61B 5/6826* (2013.01); *A61B 5/6838* (2013.01); *A61B 5/726* (2013.01); *A61B 5/7257* (2013.01); *A61B 5/7203* (2013.01)

(58) Field of Classification Search
None
See application file for complete search history.

(56) References Cited

U.S. PATENT DOCUMENTS

| | | | |
|---|---|---|---|
| 4,625,731 A | 12/1986 | Quedens et al. | |
| 5,341,806 A | 8/1994 | Gadsby et al. | |
| 5,431,170 A | 7/1995 | Mathews | |
| 5,673,692 A | 10/1997 | Schulze et al. | |
| 6,615,065 B1* | 9/2003 | Barrett | A61B 5/14553 600/323 |
| 7,496,400 B2 | 2/2009 | Hoskonen et al. | |
| 9,138,183 B2 | 9/2015 | McKenna et al. | |
| 9,517,024 B2* | 12/2016 | Kiani | A61B 5/0205 |
| 2003/0199770 A1 | 10/2003 | Chen et al. | |
| 2003/0225323 A1* | 12/2003 | Kiani | A61B 5/0478 600/323 |
| 2003/0236452 A1 | 12/2003 | Melker et al. | |
| 2004/0019293 A1 | 1/2004 | Schweitzer, Jr. et al. | |
| 2005/0004489 A1 | 1/2005 | Sarkela et al. | |
| 2005/0096513 A1 | 5/2005 | Ozguz et al. | |
| 2005/0131288 A1 | 6/2005 | Turner et al. | |
| 2007/0100219 A1 | 5/2007 | Sweitzer et al. | |
| 2007/0123756 A1 | 5/2007 | Kitajima et al. | |
| 2007/0167694 A1 | 7/2007 | Causevic et al. | |
| 2008/0015424 A1 | 1/2008 | Bernreuter | |
| 2008/0027502 A1* | 1/2008 | Ransom | A61B 5/036 607/42 |
| 2008/0071328 A1* | 3/2008 | Haubrich | A61B 5/0031 607/60 |
| 2008/0082137 A1* | 4/2008 | Kieval | A61N 1/0551 607/30 |
| 2008/0281180 A1 | 11/2008 | Choe et al. | |
| 2009/0105605 A1 | 4/2009 | Abreu | |
| 2009/0281403 A1 | 11/2009 | Benni | |
| 2010/0130840 A1 | 5/2010 | Isaacson | |
| 2010/0210924 A1 | 8/2010 | Parthasarathy et al. | |
| 2010/0312079 A1* | 12/2010 | Larsen | A61B 5/14551 600/323 |
| 2010/0324389 A1 | 12/2010 | Moon et al. | |
| 2018/0160915 A1 | 6/2018 | McKenna et al. | |

FOREIGN PATENT DOCUMENTS

WO  2005074807 A1  8/2005
WO  WO 2006/090371  8/2006
WO  WO 2009/033181  3/2009

OTHER PUBLICATIONS

Examination Report from counterpart Australian Application No. 2011212903, dated Dec. 17, 2012, 4 pp.

(Continued)

*Primary Examiner* — Anna Skibinsky

(57) ABSTRACT

A combined physiological sensor and methods for detecting one or more physiological characteristics of a subject are provided. The combined sensor (e.g., a forehead sensor) may be used to detect and/or calculate at least one of a pulse blood oxygen saturation level, a regional blood oxygen saturation level, a respiration rate, blood pressure, an electrical physiological signal (EPS), a pulse transit time (PTT), body temperature associated with the subject, a depth of consciousness (DOC) measurement, any other suitable physiological parameter, and any suitable combination thereof. The combined sensor may include a variety of individual sensors, such as electrodes, optical detectors, optical emitters, temperature sensors, and/or other suitable sensors. The sensors may be advantageously positioned in accordance with a number of different geometries. The combined sensor may also be coupled to a monitoring device, which may receive and/or process one or more output signals from the individual sensors to display information about the medical condition of the subject. In addition, several techniques may be employed to prevent or limit interference between the individual sensors and their associated input and/or output signals.

20 Claims, 11 Drawing Sheets

(56) References Cited

OTHER PUBLICATIONS

Examination Report from counterpart European Application No. 11705336.3, dated Oct. 2, 2015, 3 pp.
Response to Examination Report dated Oct. 2, 2015, from counterpart European Application No. 11705336.3, filed Jan. 15, 2016, 21 pp.
Notice of Intent to Grant and Text Intended to Grant from counterpart European Application No. 11705336.3, dated Jun. 12, 2018, 104 pp.
International Search Report and Written Opinion of International Application No. PCT/US2011/023630, dated Apr. 29, 2011, 10 pp.
International Preliminary Report on Patentability from International Application No. PCT/US2011/023630, dated Aug. 7, 2012, 7 pp.
Prosecution History from U.S. Appl. No. 13/020,704, dated May 23, 2012, through Jun. 25, 2015, 190 pp.
Examination Report from counterpart European Application No. 11705336.3, dated Oct. 19, 2016, 3 pp.
Response to Examination Report dated Oct. 19, 2016, from counterpart European Application No. 11705336.3, filed Apr. 17, 2017, 13 pp.
Response to Examination Report dated Dec. 17, 2012, from counterpart Australian Application No. 2011212903, filed Sep. 5, 2014, 14 pp.
Examination Report from counterpart Australian Application No. 2011212903, dated Sep. 9, 2014, 4 pp.
Examination Report from counterpart Canadian Application No. 2,787,471 dated Jul. 7, 2014, 3 pp.
Response to Examination Report dated Jul. 7, 2014, from counterpart Canadian Application No. 2,787,471, filed Jan. 6, 2015, 18 pp.

* cited by examiner under consideration of the following detailed description, taken in

COMBINED PHYSIOLOGICAL SENSOR SYSTEMS AND METHODS

CROSS-REFERENCE TO RELATED APPLICATIONS

This application is a continuation of U.S. patent application Ser. No. 13/020,704, filed Feb. 3, 2011, which claims the benefit of U.S. Provisional Patent Application No. 61/301,088, filed Feb. 3, 2010, both of which are hereby incorporated by reference herein in their entireties.

SUMMARY

The present disclosure relates to sensors and, more particularly, to combined physiological sensors and methods for detecting one or more physiological characteristics of a subject. A combined sensor (e.g., a forehead sensor) may be used to detect and/or calculate at least one of a pulse blood oxygen saturation level, a regional blood oxygen saturation level, a respiration rate, blood pressure, an electrical physiological signal (EPS), a pulse transit time (PTT), body temperature associated with the subject, a depth of consciousness (DOC) measurement, any other suitable physiological parameters, and any suitable combination thereof. The individual sensors within the combined sensor may be advantageously positioned in accordance with a number of different geometries. In addition, several techniques may be employed to prevent or limit interference between the individual sensors and their associated input and/or output signals. The combined sensor may be coupled to a monitoring device, which may receive and/or process one or more output signals from the individual sensors to display information about the medical condition of the subject.

In an embodiment, a physiological sensor device is provided that includes a flexible substrate capable of being applied to a subject. A first electrode may be disposed on the substrate for receiving a first electrical signal associated with the subject, and a second electrode may be disposed on the substrate for receiving a second electrical signal associated with the subject. An optical detector may be disposed on the substrate at a location between the first electrode and the second electrode for receiving an optical signal transmitted into the subject. The device, in some approaches, may additionally include an optical emitter disposed on the substrate for transmitting an optical signal into the subject.

In an embodiment, the device includes a structure coupled to the substrate that is also capable of being applied to the subject. A second optical emitter may be disposed on the structure for transmitting a second optical signal into the subject, and a second optical detector may be disposed on the structure for receiving the second optical signal. In another embodiment, the optical detector is disposed near the optical emitter and a second optical detector may be disposed on the substrate at a distance from the emitter for receiving the optical signal transmitted into the subject.

In an embodiment, the device includes a temperature sensor disposed on the substrate for detecting a temperature of the subject. Moreover, the optical detector may be disposed in a location between the optical emitter and a second optical detector, and the temperature sensor may be disposed in a location between the two optical detectors. This arrangement may substantially isolate the temperature sensor from any heat generated by the optical emitter.

In some approaches, the first electrode, the second electrode, and the optical detector are disposed on the substrate in a geometry that positions the first electrode over the center of the subject's forehead, the second electrode over the subject's temple, and the optical sensor over highly perfused tissue of the subject, when the substrate is applied to the subject. In an embodiment, the device includes a third electrode disposed on the substrate for receiving a third electrical signal associated with the subject, and a fourth electrode disposed on the substrate for receiving a fourth electrical signal associated with the subject. In this embodiment, the first electrode, the second electrode, the third electrode, and the fourth electrode may be disposed on the substrate at substantially equally spaced intervals.

In an embodiment, the output signals from the first electrode, the second electrode, and the optical detector are routed via interconnects to a shared cable connected to monitoring circuitry. In another embodiment, the device includes processing circuitry that receives the first electrical signal, the second electrical signal, and the optical signal, and calculates at least one of a pulse blood oxygen saturation level, a regional blood oxygen saturation level, a respiration rate, blood pressure, an electrical physiological signal, a pulse transit time, body temperature, and a depth of consciousness measurement.

BRIEF DESCRIPTION OF THE DRAWINGS

The above and other features of the present disclosure, its nature and various advantages will be more apparent upon consideration of the following detailed description, taken in conjunction with the accompanying drawings in which.

DETAILED DESCRIPTION

Figure 1:
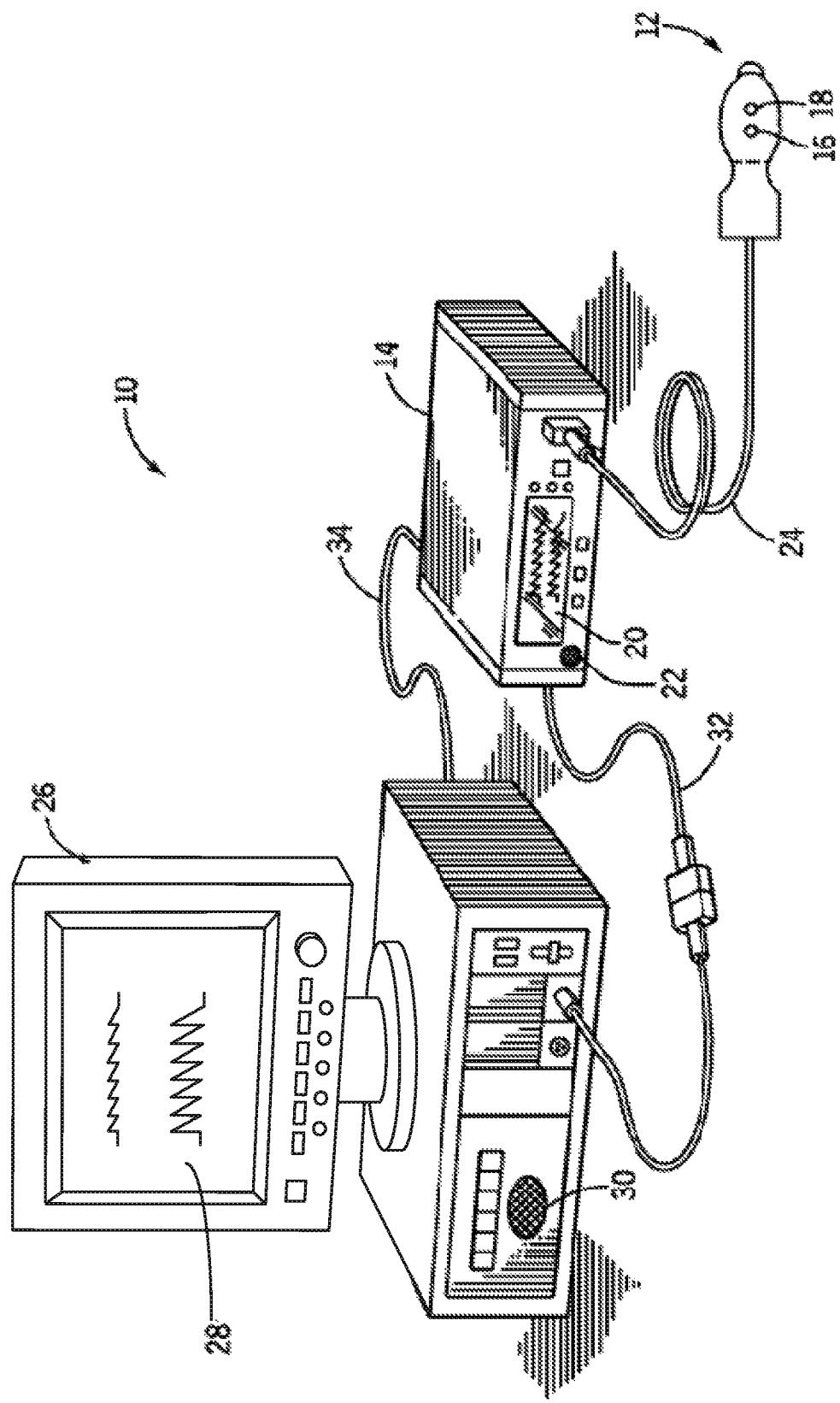
FIG. 1 is a perspective view of a monitoring system, in which one or more physiological characteristics of a subject are monitored in accordance with an embodiment.

Monitoring the physiological state of a subject, for example, by determining, estimating, and/or tracking one or more physiological parameters of the subject, may be of interest in a wide variety of medical and non-medical applications. Indications of a subject's physiological parameters obtained from sensors (e.g., photoplethysmograph sensors, electrical physiological signal sensors, and temperature sensors) can provide short-term and long-term benefits to the subject, such as early detection and/or warning of potentially harmful conditions, diagnosis and treatment of illnesses, and/or guidance for preventative medicine. Medical sensors for monitoring multiple parameters are typically connected to one or more devices (e.g., single parameter or multi parameter monitors). As used herein, the term "PPG sensor" may refer to any sensor that generates a photoplethysmograph (PPG) or equivalent signal, the term "EPS sensor" may refer to any sensor that generates an electrical physiological signal (EPS), and the term "temperature sensor" may refer to any sensor that generates a signal representative of a measured temperature.

One type of medical device that can be used to monitor the physiological state of a subject is an oximeter. An oximeter may determine the oxygen saturation of blood. An oximeter may include a light sensor (e.g., a PPG sensor) that is placed at a site on a patient, typically a fingertip, toe, forehead or earlobe, or in the case of a neonate, across a foot. The oximeter may pass light using a light source through blood perfused tissue and photoelectrically sense the absorption of light in the tissue. For example, the oximeter may measure the intensity of light that is received at the light sensor as a function of time. A signal representing light intensity versus time or a mathematical manipulation of this signal (e.g., a scaled version thereof, a log taken thereof, a scaled version of a log taken thereof, etc.) may be referred to as the photoplethysmograph (PPG) signal. In addition, the term "PPG signal," as used herein, may also refer to an absorption signal (i.e., representing the amount of light absorbed by the tissue) or any suitable mathematical manipulation thereof. The light intensity or the amount of light absorbed may then be used to calculate the amount of the blood constituent (e.g., oxyhemoglobin) being measured and other physiological parameters such as the pulse rate and when each individual pulse occurs.

The light passed through the tissue is selected to be of one or more wavelengths that are absorbed by the blood in an amount representative of the amount of the blood constituent present in the blood. The amount of light passed through the tissue varies in accordance with the changing amount of blood constituent in the tissue and the related light absorption. Red (RED) and infrared (IR) wavelengths may be used because it has been observed that highly oxygenated blood will absorb relatively less red light and more infrared light than blood with a lower oxygen saturation.

It will be understood that, as used herein, the term "light" may refer to energy produced by radiative sources and may include one or more of ultrasound, radio, microwave, millimeter wave, infrared, visible, ultraviolet, gamma ray or X-ray electromagnetic radiation. As used herein, light may also include any wavelength within the radio, microwave, infrared, visible, ultraviolet, or X-ray spectra, and that any suitable wavelength of electromagnetic radiation may be appropriate for use with the present techniques.

When the measured blood parameter is the oxygen saturation of hemoglobin, a convenient starting point assumes a saturation calculation based on Lambert-Beer's law. The following notation will be used herein:

$$I(\lambda,t)=I_o(\lambda)\exp(-(s\beta_o(\lambda)+(1-s)\beta_r(\lambda))l(t)) \quad (1)$$

where:
 $\lambda$=wavelength;
 t=time;
 I=intensity of light detected;
 $I_o$=intensity of light transmitted;
 s=oxygen saturation;
 $\beta_o$, $\beta_r$=empirically derived absorption coefficients; and
 l(t)=a combination of concentration and path length from emitter to detector as a function of time.

One common type of oximeter is a pulse oximeter, which may indirectly measure the oxygen saturation of a patient's blood (as opposed to measuring oxygen saturation directly by analyzing a blood sample taken from the patient) and changes in blood volume in the skin. In pulse oximetry, by comparing the intensities of two wavelengths at different points in the pulse cycle, it is possible to estimate the blood oxygen saturation of hemoglobin in arterial blood. Ancillary to the blood oxygen saturation measurement, pulse oximeters may also be used to measure the pulse rate of the patient. Pulse oximeters typically measure and display various blood flow characteristics including, but not limited to, the oxygen saturation of hemoglobin in arterial blood.

For example, using a pulse oximeter, saturation may be calculated by solving for the "ratio of ratios" as follows.

1. First, the natural logarithm of (1) is taken ("log" will be used to represent the natural logarithm) for IR and Red $$\log I = \log I_o - (s\beta_o + (1-s)\beta_r)l \quad (2)$$

2. (2) is then differentiated with respect to time $$\frac{d\log I}{dt} = -(s\beta_o + (1-s)\beta_r)\frac{dl}{dt} \quad (3)$$

3. Red (3) is divided by IR (3)

$$\frac{d\log I(\lambda_R)/dt}{d\log I(\lambda_{IR})/dt} = \frac{s\beta_o(\lambda_R) + (1-s)\beta_r(\lambda_R)}{s\beta_o(\lambda_{IR}) + (1-s)\beta_r(\lambda_{IR})} \quad (4)$$

4. Solving for s $$s = \frac{\frac{d\log I(\lambda_{IR})}{dt}\beta_r(\lambda_R) - \frac{d\log I(\lambda_R)}{dt}\beta_r(\lambda_{IR})}{\frac{d\log I(\lambda_R)}{dt}(\beta_o(\lambda_{IR}) - \beta_r(\lambda_{IR})) - \frac{d\log I(\lambda_{IR})}{dt}(\beta_o(\lambda_R) - \beta_r(\lambda_R))}$$

Note in discrete time $$\frac{d\log I(\lambda, t)}{dt} \simeq \log I(\lambda, t_2) - \log I(\lambda, t_1)$$

Using log A−log B=log A/B, $$\frac{d\log I(\lambda, t)}{dt} \simeq \log\left(\frac{I(t_2, \lambda)}{I(t_1, \lambda)}\right)$$

So, (4) can be rewritten as $$\frac{\frac{d\log I(\lambda_R)}{dt}}{\frac{d\log I(\lambda_{IR})}{dt}} \simeq \frac{\log\left(\frac{I(t_1, \lambda_R)}{I(t_2, \lambda_R)}\right)}{\log\left(\frac{I(t_1, \lambda_{IR})}{I(t_2, \lambda_{IR})}\right)} = R \quad (5)$$

where R represents the "ratio of ratios." Solving (4) for s using (5) gives $$s = \frac{\beta_r(\lambda_R) - R\beta_r(\lambda_{IR})}{R(\beta_o(\lambda_{IR}) - \beta_r(\lambda_{IR})) - \beta_o(\lambda_R) + \beta_r(\lambda_R)}.$$

From (5), R can be calculated using two points (e.g., PPG maximum and minimum), or a family of points. One method using a family of points uses a modified version of (5). Using the relationship $$\frac{d\log I}{dt} = \frac{dI/dt}{I} \quad (6)$$

now (5) becomes $$\frac{\frac{d\log I(\lambda_R)}{dt}}{\frac{d\log I(\lambda_{IR})}{dt}} \simeq \frac{\frac{I(t_2, \lambda_R) - I(t_1, \lambda_R)}{I(t_1, \lambda_R)}}{\frac{I(t_2, \lambda_{IR}) - I(t_1, \lambda_{IR})}{I(t_1, \lambda_{IR})}} = \quad (7)$$

$$\frac{[I(t_2, \lambda_R) - I(t_1, \lambda_R)]I(t_1, \lambda_{IR})}{[I(t_2, \lambda_{IR}) - I(t_1, \lambda_{IR})]I(t_1, \lambda_R)} = R$$

which defines a cluster of points whose slope of y versus x will give R where $$x(t) = [I(t_2, \lambda_{IR}) - I(t_1, \lambda_{IR})]I(t_1, \lambda_R)$$

$$y(t) = [I(t_2, \lambda_R) - I(t_1, \lambda_R)]I(t_1, \lambda_{IR})$$

$$y(t) = Rx(t) \quad (8)$$

Once R is determined or estimated, for example, using the techniques described above, the blood oxygen saturation can be determined or estimated using any suitable technique for relating a blood oxygen saturation value to R. For example, blood oxygen saturation can be determined from empirical data that may be indexed by values of R, and/or it may be determined from curve fitting and/or other interpolative techniques.

The foregoing is merely illustrative and any suitable processing techniques may be used to calculate pulse oximetry values. For example, Fourier transforms and continuous wavelet transforms may be used to process the PPG signals and derive blood oxygen saturation.

Another common type of oximeter is a regional oximeter, which may be used to calculate an oxygen saturation of a patient's blood in a non-invasive manner. In regional oximetry, by comparing the intensities of two wavelengths of light, it is possible to estimate the blood oxygen saturation of hemoglobin in a region of a body. Whereas pulse oximetry measures blood oxygen based on changes in the volume of blood due to pulsing tissue (e.g., arteries), regional oximetry typically examines blood oxygen saturation within the venous, arterial and capillary systems within a region of a patient. For example, a regional oximeter may include a sensor to be placed on a patient's forehead and may be used to calculate the oxygen saturation of a patient's blood within the venous, arterial and capillary systems of a region underlying the patient's forehead (e.g., in the cerebral cortex). The sensor may include two emitters (e.g., for emitting two wavelengths of light) and two detectors: one detector that is relatively "close" to the two emitters and another detector that is relatively "far" from the two emitters.

For example, if $I_A$ represents the intensity of the received/detected light associated with the "close" detector, $$\frac{I_A(\lambda, t)}{I_O(\lambda)},$$

may be derived using Lambert-Beer's law, described above. Similarly, if $I_B$ represents the intensity of the received/detected light associated with the "far" detector, $$\frac{I_B(\lambda, t)}{I_O(\lambda)},$$

may be derived using Lambert-Beer's law, described above. Light intensity of multiple wavelengths may be received at both the "close" and the "far" detectors. For example, if two wavelength were used, the two wavelengths may be contrasted at each location and the resulting signals may be contrasted to arrive at a regional saturation value that pertains to additional tissue through which the light received at the "far" detector passed (tissue in addition to the tissue through which the light received by the "close" detector passed, e.g., the brain tissue), when it was transmitted through a region of a patient (e.g., a patient's cranium). Other methods to calculate regional blood oxygen saturation are well known in the art.

Pulse blood oxygen saturation and regional blood oxygen saturation may be measured and/or calculated, in an embodiment, simultaneously. For example, in the configuration described above, in which a "close" detector is disposed near two emitters (or one emitter that can output more than one wavelength of light) and a "far" detector is disposed at some distance from the two emitters, pulse oxygen saturation may be measured using the two emitters and the "close" detector (i.e., the intensity of light received/detected at the "close" detector) while regional oxygen saturation may be measured using the two emitters and the "far" detector (i.e., the intensity of light received/detected at the "far" detector). Simultaneous measurement of pulse and regional blood oxygen saturation is described further in U.S. Provisional Patent Application No. 61/260,741, H-RM-01899 (COV-88): "Simultaneous Measurement of Pulse and Regional Blood Oxygen Saturation," filed Nov. 12, 2009, which is hereby incorporated by reference herein in its entirety.

Another type of device that can be used to monitor the physiological state of a subject is a continuous non-invasive blood pressure (CNIBP) device. A CNIBP device may be include PPG sensors affixed to a subject that allow for the determination of the subject's blood pressure, for example, using CNIBP monitoring techniques. For example, some CNIBP monitoring techniques have been developed that involve the use of two probes or sensors (e.g., PPG sensors) positioned at two different locations on a subject's body. The elapsed time, T, between the arrival of corresponding points of a pulse signal at the two locations may then be determined using the two probes or sensors. The estimated blood pressure, p, may then be related to the elapsed time, T, by $$p = a + b \cdot \ln(T) \quad (9)$$

where a and b are constants that are dependent upon the nature of the subject and the signal detecting devices. Other blood pressure equations using elapsed time may also be used.

Such a CNIBPB monitoring technique is described in Chen et al. U.S. Pat. No. 6,566,251, which is hereby incorporated by reference herein in its entirety. The technique described by Chen et al. may use two sensors (e.g., ultrasound or photoelectric pulse wave sensors) positioned at any two locations on a subject's body where pulse signals are readily detected. For example, sensors may be positioned on an earlobe and a finger, an earlobe and a toe, or a finger and a toe of a patient's body. In some approaches, a single sensor or probe location may be used to determine blood pressure, as described in U.S. patent application Ser. No. 12/242,238, filed Sep. 30, 2008, which is hereby incorporated by reference herein in its entirety. In particular, a single PPG sensor may generate a PPG signal that is analyzed to compute a time difference between two or more characteristic points of the PPG signal. This time difference may be used to calculate blood pressure on a periodic or continuous basis. Alternatively, or in addition, the area under a pulse (or a portion of the pulse) in a PPG signal may be measured and used to calculate blood pressure.

Similar sensors or probes may also be used to determine respiration rate and other respiratory properties (e.g., respiratory effort). For example, as described in more detail in Addison et al. U.S. Patent App. Pub. No. 2006/0258921, published Nov. 16, 2006, which is incorporated by reference herein in its entirety, the act of breathing may cause a breathing band to become present in a scalogram derived from a continuous wavelet transform of a PPG signal. This breathing band may occur at or about the scale having a characteristic frequency that corresponds to the breathing frequency. Furthermore, the features within this band (e.g., the energy, amplitude, phase, or modulation) or the features within other bands of the scalogram may result from changes in breathing rate (or breathing effort) and therefore may be correlated with various respiratory parameters of a patient.

Other devices and sensors may also be used to determine physiological parameters of a subject. For example, an electrical physiological signal (EPS) sensor may be used to determine such signals as electroencephalographic (EEG) signals, electrocardiography (ECG or EKG) signals, electromyography (EMG) signals, or any other electrical physiological signal. Sensors may also be used to determine a subject's body temperature, a pulse transit times (PTT), or both. In an embodiment, PTT may be determined by using PPG data in conjunction with EPS data. For example, PTT may be determined by comparing an ECG onset point with a PPG arrival point. An ECG signal may be processed in order to detect the QRS complex and to detect the R wave peak. The plethysmograph signal may be processed to detect the pulse timing. The PTT may then be calculated as the time between the R wave peak and the corresponding pulse peak. Other suitable techniques for calculating PTT are well known in the art and may also be used.

In an embodiment, sensors may be used, to determine a subject's depth of consciousness (DOC). In particular, a DOC measurement may be determined using measured PPG signals, EPS signals, or a combination thereof. For example, one or more EPS signals may be processed to supply a consciousness index, indicating a patient's depth of consciousness on a scale. As another example, a PPG signal may exhibit one or more waveform features which indicate consciousness. Techniques for monitoring/assessing depth of consciousness using physiological signals, such as PPG and EPS signals, are described in detail ire U.S. patent application Ser. No. 13/364,766 "Systems And Methods For Monitoring Depth Of Consciousness," filed Feb. 2, 2012, which is hereby incorporated by reference herein in its entirety.

These and other devices and sensors can be used for monitoring physiological parameters of a subject. The devices may be standalone devices or may be combined into one or more multi-parameter monitoring devices. The monitoring devices may be physically connected to each sensor to receive signals from the sensors and perform various processing of the signals. The physiological parameters may, for example, be consolidated and displayed on a single display to provide a condensed view of the subject's physiological state to assist a medical professional in treating the subject. Alternatively, a subject's physiological parameters obtained from the sensor signals may be displayed on multiple displays that may be associated with one or more single parameter and multiple parameter monitoring devices.

In accordance with the present disclosure, a combined physiological sensor is provided to facilitate the connection and coordination of multiple sensors with one or more monitoring devices. In particular, a combined physiological sensor may incorporate a number of physiological sensors and other components embedded within, or attached to, a sensor structure suitable for application to a subject (e.g., a human subject). This sensor structure may be flexible, such that it can bend when applied to a curved surface (e.g., a human forehead) thereby facilitating contact between the sensor structure, or the sensors, and the curved surface. The sensor structure may also include an adhesive to secure the combined physiological sensor to the subject, further aiding contact between the sensor structure or sensors and the surface of application. In addition, the sensor structure may contain or be attached to circuitry for connecting the sensors to a cable, wireless transmitter, memory device or other means for storing and/or transmitting data generated by the sensors to a monitor. For example, the sensor structure may be a flex circuit, in which the sensors, interconnections, and other electronic devices may be mounted, deposited, and/or printed onto a flexible substrate. The composition, shape, and other details related to the sensor structure will be discussed further below.

Integrating multiple sensors into a combined physiological sensor in accordance with the present disclosure provides numerous advantages over traditional sensor and monitoring systems. In particular, a combined physiological sensor may require fewer cables and components than the traditional approach in order to support multiple sensors, which in turn helps reduce cost and total sensor area. In a traditional system, for example, each sensor applied to a patient may include its own cable connection to one or more monitoring devices; supporting a number of sensors may therefore involve the use of numerous cables and/or other supporting equipment. A combined physiological sensor, however, may unite multiple sensors within one or more sensor structures and may route all or some sensor output signals to a shared cable connected to one or more monitors. In addition to the simplification, minimization, and cost-reduction offered by a single-cable or reduced number of cables approach, reducing the number of cables necessary to deliver data to a monitoring device mitigates the potential for entanglement or human error involved in connecting the cables appropriately. Furthermore, a combined physiological sensor with a sensor structure that integrates multiple sensors in a particular geometry, may facilitate proper placement of sensors relative to a patient and relative to other sensors. For example, each sensor applied to a patient may require disposition within a specific area of the patient's body. Moreover, when applying multiple sensors to a patient, care may be required to avoid or reduce interference between the sensors and/or their respective input or output signals. As such, in a traditional approach, each sensor applied to a patient may require a laborious process of sensor site identification and application while simultaneously demanding consideration of other sensor locations. A combined physiological sensor, on the other hand, may integrate multiple sensors in a specific geometry, such that proper placement of the combined physiological sensor results in proper disposition of the individual sensors on the patient. The combined physiological sensor may also be configured, as discussed below, to reduce or limit interference between the individual sensors and/or their associated signals. Sensor integration and interference reduction, among other objects of the present disclosure, are more fully discussed in the description that follows in connection with FIGS. 1-8.

FIG. 1 is a perspective view of an embodiment of a monitoring system 10. System 10 may include a sensor 12 and a monitor 14. Sensor 12 may include one or more emitters 16 for emitting light at two or more wavelengths into a patient's tissue. One or more detectors 18 may also be provided in sensor 12 for detecting the light originating from emitters 16 that either passes through the patient's tissue or reflects off one or more surfaces of the tissue.

In accordance with the present disclosure, system 10 may include a plurality of sensors—such as PPG sensors (e.g., oximetry and/or CNIBP sensors), EPS sensors (e.g., ECG, EEG, and/or EMG sensors), and temperature sensors— forming a combined physiological sensor in lieu of single sensor 12. It should be understood that although the description below, in connection with FIG. 1, refers primarily to single sensor 12, a combined physiological sensor may be substituted to augment the capabilities of system 10. It should further be understood that the description of system 10, and in particular the description of the various embodiments and configurations thereof, is equally applicable when a combined physiological sensor is used in lieu of single sensor 12. Specifically, all interconnections, cables, components, and/or modes of communication may remain substantially the same and/or serve substantially the same purposes. The combined physiological sensor may be of any configuration and composition, as discussed herein further below. In particular, the combined physiological sensor may be any of those described in connection with FIG. 4A (i.e., sensor 410), FIG. 4B (i.e., sensor 420), FIG. 4C (i.e., sensor 430), FIG. 4D (i.e., sensor 440), FIG. 5 (i.e., sensor 510), FIG. 6A (i.e., sensor 610), FIG. 6B (i.e., sensor 620), FIG. 6C (i.e., sensor 630), and FIG. 7A and FIG. 7B (i.e., sensor 710).

Each EPS sensor of the combined physiological sensor may include a passive or active electrode. The EPS sensors may be any suitable device for detecting voltages, currents, or impedances. The temperature sensors may be any suitable temperature measurement device, including devices that measure temperature through direct contact and those that measure temperature without direct contact (e.g., through detection of thermal radiation). Each of the PPG sensors of the combined physiological sensor may be a complementary metal oxide semiconductor (CMOS) sensor or a charged coupled device (CCD) sensor. In another embodiment, the combined physiological sensor may be made up of a combination of CMOS and CCD sensors. The CCD sensors may comprise a photoactive region and a transmission region for receiving and transmitting data whereas the CMOS sensors may be made up of an integrated circuit having an array of pixel sensors. Each pixel may have a photodetector and an active amplifier.

According to an embodiment, emitters 16 and detectors 18 of sensor 12 may be on opposite sides of a section of tissue (e.g., within a digit such as a finger or toe), in which case the light detected by detectors 18 has passed completely through the tissue. In another embodiment, emitters 16 and detectors 18 may be positioned on the same side of a section of tissue (e.g., within the forehead) so that light from emitters 16 is reflected by the tissue into detectors 18.

In an embodiment, sensor 12, or the sensors included in a combined physiological sensor, may be connected to and draw power from monitor 14 through cable 24 as shown. In another embodiment, the sensors may be wirelessly connected to monitor 14 and draw power from a battery or similar power supply (not shown). Monitor 14 may be configured to calculate physiological parameters based at least in part on data received from sensor 12, or the sensors of the combined physiological sensor, such as data relating to light emission and detection. In an alternative embodiment, the calculations may be performed using circuitry embedded in sensor 12, or in the combined physiological sensor, and the result of the calculations may be passed to monitor 14. Further, monitor 14 may include a display 20 configured to display the physiological parameters or other information about the system. In the embodiment shown, monitor 14 may also include a speaker 22 to provide an audible sound that may be used in various other embodiments, such as for example, sounding an audible alarm in the event that a patient's physiological parameters are not within a predefined normal range.

In the embodiment depicted in FIG. 1, sensor 12, or the combined physiological sensor, is communicatively coupled to monitor 14 via a cable 24. However, in another embodiment, a wireless transmission device (not shown) or the like may be used instead of, or in addition to, cable 24. In an embodiment, sensor 12, or the combined physiological sensor, may incorporate a storage device for recording data produced by the sensors. The stored data may be transmitted to monitor 14 at a later time, for example, via cable 24 or a wireless transmission device, or the storage device may be disconnected from the sensor and connected directly to monitor 14.

In the illustrated embodiment, monitoring system 10 may also include a multi-parameter patient monitor 26. The monitor may be cathode ray tube type, a flat panel display (as shown) such as a liquid crystal display (LCD) or a plasma display, or any other type of monitor now known or later developed. Multi-parameter patient monitor 26 may be configured to calculate physiological parameters and to provide a display 28 for information from monitor 14 and from other medical monitoring devices or systems (not shown). For example, multiparameter patient monitor 26 may be configured to display an estimate of a patient's pulse blood oxygen saturation (referred to as an "$SpO_2$" measurement), regional blood oxygen saturation (referred to as a "regional saturation" measurement), pulse rate, blood pressure, respiration rate, body temperature, depth of consciousness, and/or other physiological information, each generated by monitor 14 or one or more other monitoring devices, on display 28. In an embodiment, monitor 14 may itself be configured to provide blood oxygen saturation, regional blood oxygen saturation, pulse rate, blood pressure, respiration rate, body temperature, depth of consciousness, and/or other physiological information on display 20 or to monitor 26.

Monitor 14 may be communicatively coupled to multi-parameter patient monitor 26 via a cable 32 or 34 that is coupled to a sensor input port or a digital communications port, respectively and/or may communicate wirelessly (not shown). In addition, monitor 14 and/or multi-parameter patient monitor 26 may be coupled to a network to enable the sharing of information with servers or other workstations (not shown). Monitor 14 may be powered by a battery (not shown) or by a conventional power source such as a wall outlet.

Figure 2:
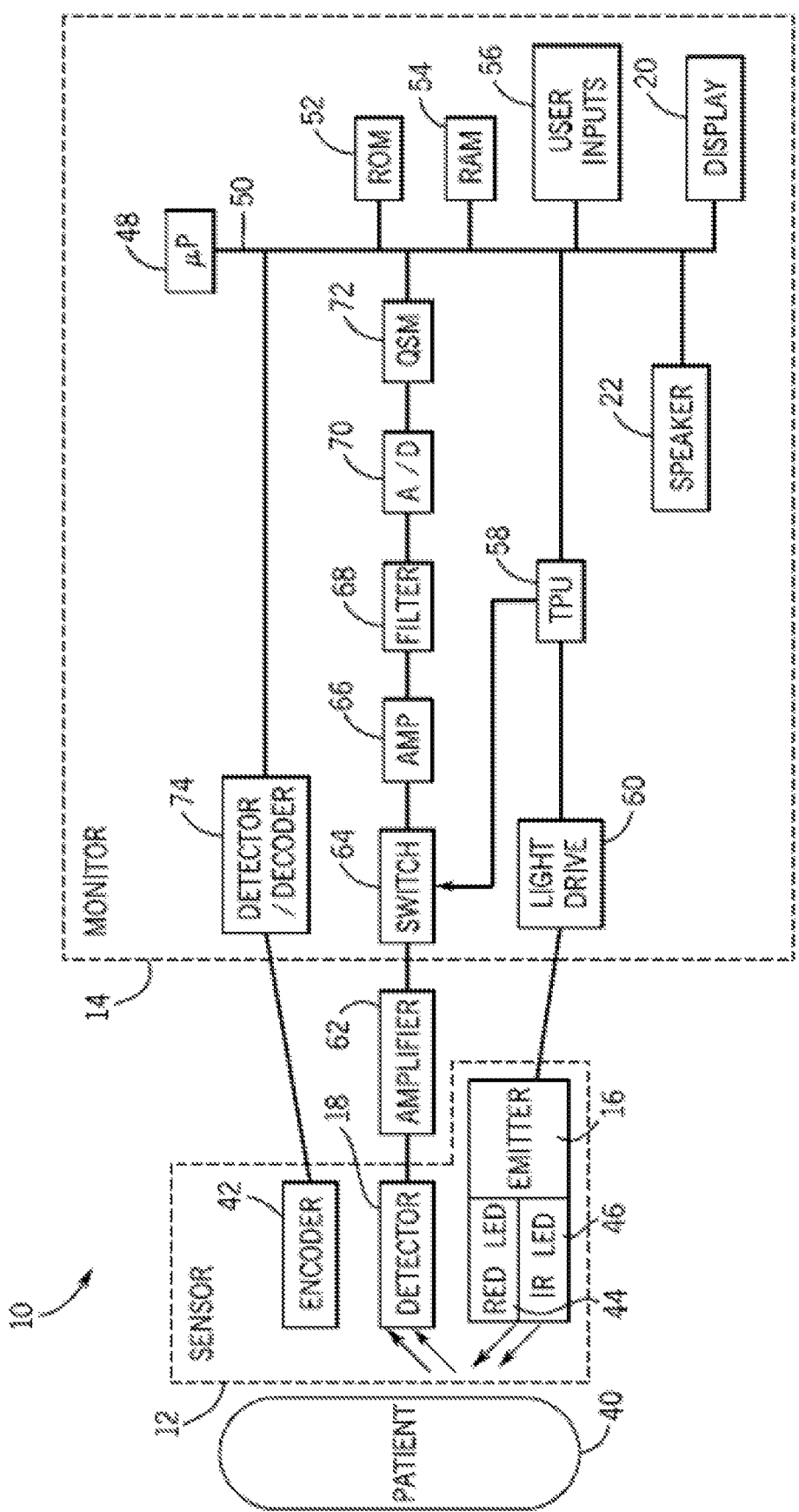
FIG. 2 is a block diagram of a monitoring system, such as the system depicted in FIG. 1, coupled to a patient in accordance with an embodiment.

FIG. 2 is a block diagram of a monitoring system, such as system 10 of FIG. 1, which may be coupled to a patient 40 in accordance with an embodiment. Certain illustrative components of sensor 12 and monitor 14 are illustrated in FIG. 2. Sensor 12 may include emitters 16, detectors 18, and encoder 42. Alternatively, as discussed above in connection with FIG. 1, system 10 may include a plurality of sensors—such as PPG sensors (e.g., oximetry and/or CNIBP sensors), EPS sensors (e.g., ECG, EEG, and/or EMG sensors), and temperature sensors—in a combined physiological sensor in lieu of single sensor 12. It should be understood that although the description below, in connection with FIG. 2, refers primarily to single sensor 12, a combined physiological sensor may be substituted instead. In particular, the description of the various embodiments and configurations of system 10, as it relates to sensor 12, may be extended to embodiments in which combined physiological sensor is used in lieu of sensor 12. Specifically, all interconnections, cables, components, and/or modes of communication may remain substantially the same and/or serve substantially the same purposes. The combined physiological sensor may be of any configuration and composition, as discussed herein further below. In particular, the combined physiological sensor may be any of those described in connection with FIG. 4A (i.e., sensor 410), FIG. 4B (i.e., sensor 420), FIG. 4C (i.e., sensor 430), FIG. 4D (i.e., sensor 440), FIG. 5 (i.e., sensor 510), FIG. 6A (i.e., sensor 610), FIG. 6B (i.e., sensor 620), FIG. 6C (i.e., sensor 630), and FIG. 7A and FIG. 7B (i.e., sensor 710).

In the embodiment shown, emitters 16 may be configured to emit at least two wavelengths of light (e.g., RED and IR) into a patient's tissue 40. Hence, emitters 16 may include a RED light emitting light source such as RED light emitting diode (LED) 44 and an IR light emitting light source such as IR LED 46 for emitting light into the patient's tissue 40 at the wavelengths used to calculate the patient's physiological parameters. In one embodiment, the RED wavelength may be between about 600 nm and about 700 nm, and the IR wavelength may be between about 700 nm and about 1000 nm. When multiple light emitting sensors are provided (e.g., in a combined physiological sensor that includes multiple PPG sensors), each light emitting sensor may be configured to emit one or more wavelengths of light. Detectors 18 may be chosen to be specifically sensitive to the chosen targeted energy spectrum of the emitters 16.

In an embodiment, detectors 18 may be configured to detect the intensity of light at both the RED and IR wavelengths. Detectors 18 may include individual detecting elements each configured to detect an intensity of a single wavelength. In operation, light may enter detectors 18 after passing through the patient's tissue 40. Detectors 18 may convert the intensity of the received light into an electrical signal. The light intensity is directly related to the absorbance and/or reflectance of light in the tissue 40. That is, in cases where emitters 16 and detectors 18 are on opposite sides of a patient's tissue, less light of a particular wavelength is received by the detectors 18 when more light at the particular wavelength is absorbed or reflected by the tissue. Alternatively, in cases where emitters 16 and detectors 18 are on the same side of a patient's tissue, less light of a particular wavelength is received by the detectors 18 when more light at the particular wavelength passes through or is absorbed by the tissue. After converting the received light to an electrical signal, detectors 18 may send the signal to monitor 14, where physiological parameters may be calculated based on the detected intensity of the RED and IR wavelengths.

In an embodiment, encoder 42 may contain information about sensor 12, or the combined physiological sensor, such as what type of sensor it is (e.g., whether the sensor is intended for placement on a forehead or digit) and the wavelengths of light emitted by emitters 16. In cases of a combined physiological sensor, encoder 42 may additionally include information on the types and number of sensors included, as well as identification data enabling direct communication with one or more of the sensors. The information contained within encoder 42 may be used by monitor 14 to select appropriate algorithms, lookup tables, and/or calibration coefficients stored in monitor 14 for calculating the patient's physiological parameters. In addition, the information contained within encoder 42 may be used by monitor 14, or by processing circuitry within the combined physiological sensor itself, to select, configure, or communicate with one or more sensors in the combined physiological sensor.

Encoder 42 may contain information specific to patient 40, such as, for example, the patient's age, weight, and diagnosis. This information may allow monitor 14 to determine, for example, patient-specific threshold ranges in which the patient's physiological parameter measurements should fall and to enable or disable additional physiological parameter algorithms. Encoder 42 may, for instance, be a coded resistor which stores values corresponding to the type of sensor 12, or the types of each sensor in the combined physiological sensor, the wavelengths of light emitted by emitters 16, the predefined positioning of the sensors on the patient, and/or the patient's characteristics. In another embodiment, encoder 42 may include a memory on which one or more of the following information may be stored for communication to monitor 14: the type of the sensor 12 or the type of each sensor in the combined physiological sensor; the wavelengths of light emitted by emitters 16; the particular wavelength each of the detectors 18 is monitoring; a signal threshold for each sensor in the combined physiological sensor; the predefined positioning of the sensors in the combined physiological sensor on the patient, any other suitable information; or any combination thereof. Sensor type information may include an indication that a sensor is a PPG, EPS, temperature, or other sensor. Sensor type information may also specify whether a given PPG sensor is a pulse or regional blood oxygen saturation sensor, a CNIPB sensor, or a respiration sensor; whether a given EPS sensor is an EEG, ECG, or EMG sensor; and/or any other sensor identification information.

In an embodiment, signals from detectors 18 and encoder 42 may be transmitted to monitor 14. In the embodiment shown, monitor 14 may include a general-purpose microprocessor 48 connected to an internal bus 50. Microprocessor 48 may be adapted to execute software, which may include an operating system and one or more applications, as part of performing the functions described herein. Also connected to bus 50 may be a read-only memory (ROM) 52, a random access memory (RAM) 54, user inputs 56, display 20, and speaker 22.

RAM 54 and ROM 52 are illustrated by way of example, and not limitation. Any suitable computer-readable media may be used in the system for data storage. Computer-readable media are capable of storing information that can be interpreted by microprocessor 48. This information may be data or may take the form of computer-executable instructions, such as software applications, that cause the microprocessor to perform certain functions and/or computer-implemented methods. Depending on the embodiment, such computer-readable media may include computer storage media and communication media. Computer storage media may include volatile and non-volatile, removable and non-removable media implemented in any method or technology for storage of information such as computer-readable instructions, data structures, program modules or other data. Computer storage media may include, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by components of the system.

In the embodiment shown, a time processing unit (TPU) 58 may provide timing control signals to a light drive circuitry 60, which may control when emitters 16 are illuminated and multiplexed timing for the RED LED 44 and the IR LED 46. TPU 58 may also control the gating-in of signals from detectors 18 through an amplifier 62 and a switching circuit 64. These signals are sampled at the proper time, depending upon which light source is illuminated. The received signals from detectors 18 may be passed through an amplifier 66, a low pass filter 68, and an analog-to-digital converter 70. The digital data may then be stored in a queued serial module (QSM) 72 (or buffer) for later downloading to RAM 54 as QSM 72 fills up. In one embodiment, there may be multiple separate parallel paths having amplifier 66, filter 68, and A/D converter 70 for multiple light wavelengths or spectra received.

In an embodiment, microprocessor 48 may determine the patient's physiological parameters, such as $SpO_2$, regional oxygen saturation, pulse rate, temperature, blood pressure, respiration rate, and depth of consciousness using various algorithms and/or look-up tables based on the value of the received signals and/or data corresponding to the received signals (e.g., light received by detectors 18, electrical signals detected by EPS sensors, or temperature measured by temperature sensors). Signals corresponding to information about patient 40 (e.g., the intensity of light emanating from a patient's tissue over time) may be transmitted from encoder 42 to a decoder 74. These signals may include, for example, encoded information relating to patient characteristics. Decoder 74 may translate these signals to enable the microprocessor to determine the thresholds based on algorithms or look-up tables stored in ROM 52. User inputs 56 may be used to enter information about the patient, such as age, weight, height, diagnosis, medications, treatments, and so forth. In an embodiment, display 20 may exhibit a list of values which may generally apply to the patient, such as, for example, age ranges or medication families, which the user may select using user inputs 56.

An optical signal that passes through the tissue can be degraded by noise, among other sources. One source of noise is ambient light that reaches a light detector. Another source of noise is electromagnetic coupling from other electronic instruments or other sensors. Movement of the patient also introduces noise and affects the signal. For example, the contact between a detector and a patient's skin, or an emitter and the skin, can be temporarily disrupted when movement causes either to move away from the skin. In addition, because blood is a fluid, it responds differently than the surrounding tissue to inertial effects, thus resulting in momentary changes in volume at the point to which an oximeter probe, for example, is attached.

Noise (e.g., from patient movement) can degrade a pulse oximetry signal or other physiological signal relied upon by a physician, without the physician's awareness. This is especially true if the monitoring of the patient is remote, the motion is too small to be observed, or the doctor is watching the instrument or other parts of the patient, and not the sensor site. Processing oximetry (i.e., PPG) signals, EPS signals, temperature signals, and other physiological signals may involve operations that reduce the amount of noise present in the signals or otherwise identify noise components in order to prevent them from affecting measurements of physiological parameters derived from the physiological signals. Other techniques for reducing noise in physiological signals will be discussed below.

It will be understood that the present disclosure is applicable to any suitable signal or sensor, physiological or otherwise, that can be incorporated into a combined sensor structure. Those skilled in the art will recognize that the present disclosure has wide applicability to signals including, but not limited to biosignals (e.g., electrocardiogram, electroencephalogram, electrogastrogram, electromyogram, heart rate signals, pathological sounds, ultrasound, or any other suitable biosignal), dynamic signals, non-destructive testing signals, condition monitoring signals, fluid signals, electrical signals, sound and speech signals, chemical signals, and/or any other suitable signal, and/or any combination thereof. Similarly, those skilled in the art will recognize that the present disclosure has wide applicability to sensors including those necessary for detecting and/or monitoring any of the signals identified above.

Returning to FIG. 2, in addition, or alternatively, to providing timing control signals to a light drive circuitry 60, TPU 58 may be used to control some or all of the individual sensors within a combined physiological sensor. Accordingly, when sensor 12 is replaced with a combined physiological sensor, TPU 58 may be connected directly, or through other control circuitry, to each of the sensors of the combined physiological sensor. TPU 58 may be configured to control or activate each individual sensor, or groups of sensors acting in concert. For example, TPU 58 may control or activate one or more PPG sensors for a certain period of time, one or more temperature sensors for another period of time, and one or more EPS sensors for yet another period of time. Control and activation timing of individual sensors incorporated into a combined physiological sensor will be discussed in greater detail below in connection with FIG. 8.

Figure 3:
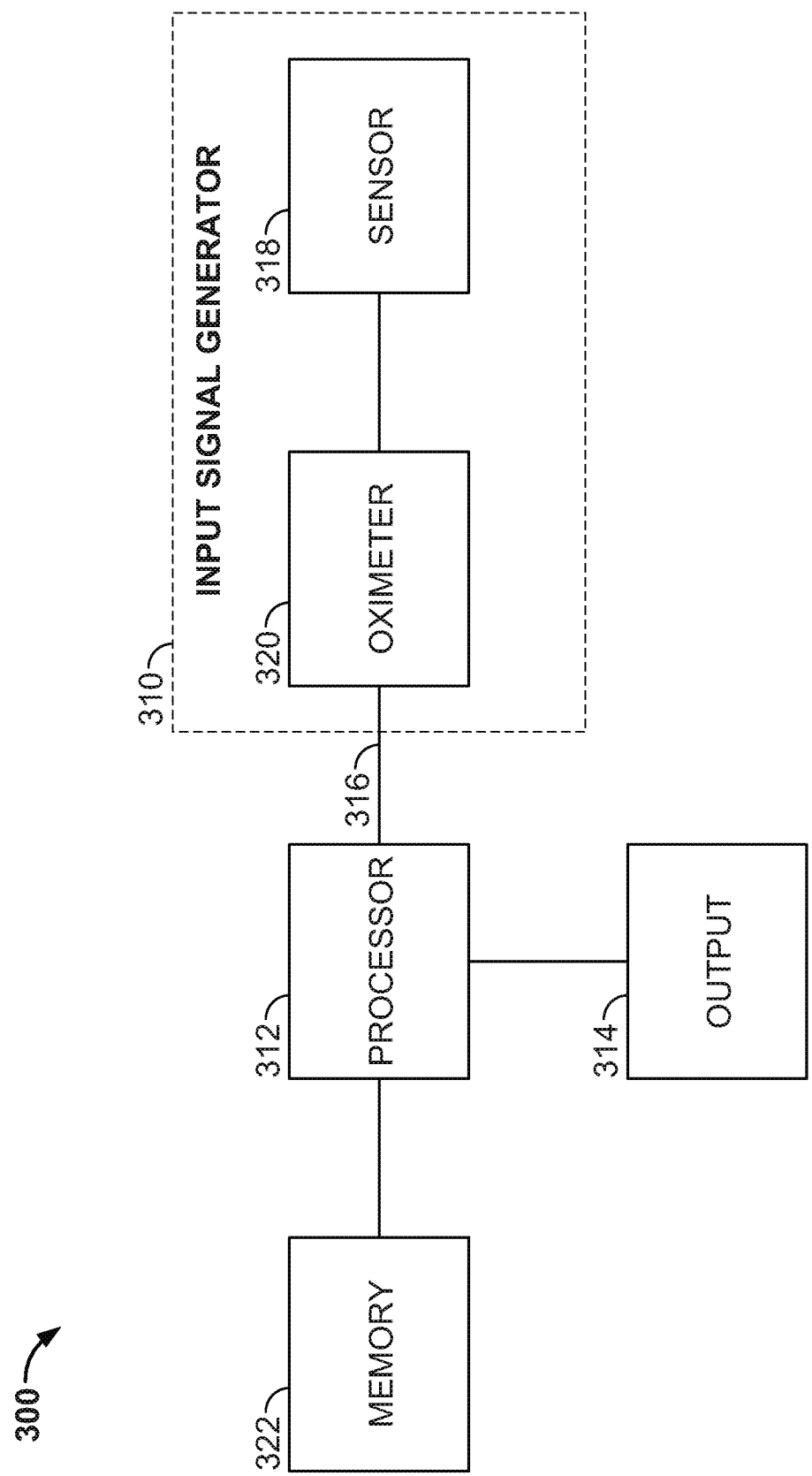
FIG. 3 is a block diagram of an illustrative sensor signal measurement system in accordance with an embodiment.

FIG. 3 is an illustrative sensor signal measurement system 300 in accordance with an embodiment. System 300 includes input signal generator 310, which generates an input signal 316. As illustrated, input signal generator 310 may include oximeter 320 coupled to sensor 318, which may provide as input signal 316, a PPG signal. It will be understood that input signal generator 310 may include any suitable signal source, signal generating data, signal generating equipment, or any combination thereof to produce signal 316. For example, sensor 318 may be a PPG, EPS, or temperature sensor and oximeter 320 may not be present in the system. Accordingly, signal 316 may be any suitable signal or signals, such as, for example, an EPS signal, a temperature signal, and/or any other suitable signal, and/or any combination thereof.

In the depicted embodiment, signal 316 may be coupled to processor 312. Processor 312 may be any suitable software, firmware, and/or hardware, and/or combinations thereof for processing signal 316. For example, processor 312 may include one or more hardware processors (e.g., integrated circuits), one or more software modules, computer-readable media such as memory, firmware, or any combination thereof. Processor 312 may, for example, be a computer or may be one or more chips (i.e., integrated circuits). Processor 312 may perform the calculations associated with continuous wavelet transforms as well as the calculations associated with any suitable interrogations of the transforms. Processor 312 may perform any suitable signal processing (including pre-processing) of signal 316 to filter signal 316, such as any suitable band-pass filtering, adaptive filtering, closed-loop filtering, and/or any other suitable filtering, and/or any combination thereof.

Processor 312 may be coupled to one or more memory devices 322 or incorporate one or more memory devices such as any suitable volatile memory device (e.g., RAM, registers, etc.), non-volatile memory device (e.g., ROM, EPROM, magnetic storage device, optical storage device, flash memory, etc.), or both. The memory may be used by processor 312 to, for example, store data corresponding to the processed input signal 316, such as data representing a scalogram generated using a continuous wavelet transform. In one embodiment, data representing the scalogram may be stored in RAM or memory internal to processor 312 as any suitable three-dimensional data structure such as a three-dimensional array that represents the scalogram as energy levels in a time-scale plane. Any other suitable data structure may be used to store data representing a scalogram.

Processor 312 may be coupled to output 314. Output 314 may be any suitable output device such as, for example, one or more medical devices (e.g., a medical monitor that displays various physiological parameters, a medical alarm, or any other suitable medical device that either displays physiological parameters or uses the output of processor 312 as an input), one or more display devices (e.g., monitor, PDA, mobile phone, any other suitable display device, or any combination thereof), one or more audio devices, one or more memory devices (e.g., hard disk drive, flash memory, RAM, optical disk, any other suitable memory device, or any combination thereof), one or more printing devices, any other suitable output device, or any combination thereof.

In an embodiment, sensor 318 may be a combined physiological sensor integrating multiple sensors, such as PPG, EPS, and temperature sensors. In one approach, processor 312 and memory 322 may be located within the combined physiological sensor. In another approach, processor 312 and memory 322 may be located within output 314 (e.g., monitor 14 of FIG. 1). In yet another approach, both the combined physiological sensor and the output device (i.e., output 314) may contain processing circuitry and/or a memory device. The combined physiological sensor and output 314 may also exchange data or signals in order to, among other activities, enable/disable individual sensors within the combined physiological sensor and process/store sensor output signals.

Figure 4A:
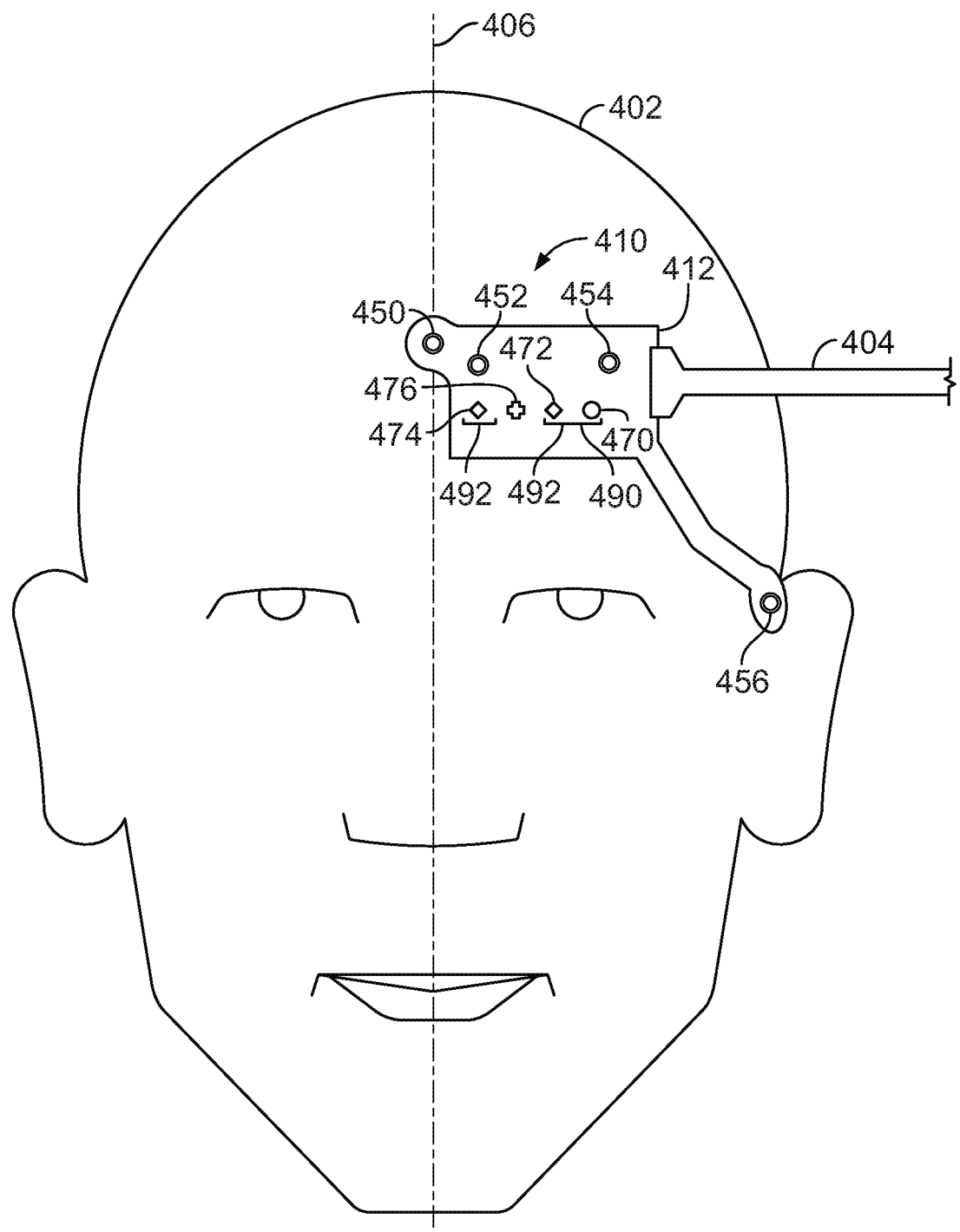
FIGS. 4A-4D show illustrative combined physiological sensors with differing geometries applied to a subject in accordance with some embodiments.

FIG. 4A shows an illustrative combined physiological sensor 410 attached to a subject 402, in accordance with an embodiment. Combined physiological sensor 410 includes a sensor structure 412, a pulse blood oxygen saturation sensor 490, a regional blood oxygen saturation sensor 492, a temperature sensor 476, and a number of EEG sensors (i.e., sensors 450, 452, 454, and 456). While FIGS. 4-7 and the accompanying description refer to EEG sensors, it should be understood that the EEG sensors may be any type of EPS sensors, including ECG and EMG sensors. Furthermore, while the arrangements depicted in FIGS. 4-7 show or refer to a combined physiological sensor including four EEG sensors, in other arrangements, fewer or more EEG sensors may be included. Similarly, it should be understood that fewer or more temperature and PPG sensors (e.g., oximetry or CNIBP sensors) may be included in the combined physiological sensors depicted in FIGS. 4-7.

Returning to the arrangement of FIG. 4A, cable 404 connects to combined physiological sensor 410 to transmit data generated by the combined physiological sensor to a monitor or data storage device (e.g., monitor 14 of FIG. 1 or output 314 of FIG. 3). Although FIG. 4 includes cable 404, it should be understood that a wireless transmitter (not shown) or a memory device (e.g., memory 322 of FIG. 3) may be used instead of a cable to transmit or store data generated by the combined physiological sensor. Moreover, these components (i.e., the wireless communications device or memory device) may be attached to or embedded within sensor structure 412 along with the individual sensors of combined physiological sensor 410. Cable 404 (or a wireless receiver) may also deliver signals generated, for example, by a monitor or other controlling device (e.g., a sensor hub) to combined physiological sensor 410. Cable 404 may contain separate sets of wires or transmission paths for delivering signals to and receiving signals from combined physiological sensor 410. Alternatively, the same set of wires or transmission paths may be used for data delivery and reception. The wires or transmission paths in cable 404 may be composed of conductive and/or fiber optic material. It should be understood that while the arrangements depicted in FIGS. 4-7 show or refer to a single cable for delivering signals to and from the combined physiological sensor, in other arrangements, additional cables may be provided. For example, a separate cable may be used for each individual sensor or groups of sensors (e.g., for each group of PPG, EPS, and temperature sensors) in the combined physiological sensor.

Generally speaking, sensor positioning for optimal detection of blood oxygen saturation and EEG signals from a subject may be different, and may vary between subjects. In the arrangement depicted in FIG. 4A, EEG sensor 450 is positioned over the horizontal center of the forehead of subject 402, EEG sensors 452 and 454 are positioned to the side of EEG sensor 450, and EEG sensor 456 is positioned over the temple of subject 402 closest to the other EEG sensors. In the depicted arrangement, EEG sensor 456 is shown incorporated into the same sensor structure (i.e., structure 412) as the other sensors. In other arrangements, however, EEG sensor 456 may part of a second sensor structure (e.g., flex circuit) that connects to sensor structure 412 via cable or other flexible connection means, or EEG sensor 456 may communicate with a wireless receiver (not shown) on sensor structure 412, or within cable 404, via a wireless transmitter (not shown). In yet other arrangements, EEG sensor 456 may connect directly to the monitoring station or to an offshoot connector of cable 404.

In the arrangement depicted in FIG. 4A, emitter 470 and detectors 472 and 474 are positioned below the EEG sensors, above the eyebrow of subject 402. Emitter 470 and detectors 472 and 474 may be positioned in alternative locations, although sites of highly perfused tissue (such as the forehead, above the eyebrow) are typically best for measuring blood oxygen saturation. As shown, pulse blood oxygen saturation sensor 490 includes emitter 470 and detector 472, while regional blood oxygen saturation sensor 492 also includes detector 474. In this arrangement, an emitter and two detectors may be used combinatorially to integrate the functionality of a pulse oxygen saturation sensor (i.e., an SpO2 sensor) and a regional oxygen saturation sensor. In particular, light from emitter 470 is transmitted into subject 402 where it reflects off one or more internal substances (e.g., tissues). A portion of this reflected light may be received at detector 472, and the measured light intensity can be used to calculate pulse oxygen saturation using, for example, the ratio of ratios technique described above or any other suitable technique. A portion of the reflected light may also be received at detector 474, and the measured light intensity can be used along with the light intensity measured by detector 472 to calculate regional oxygen saturation, as described above. In this arrangement, detector 472 serves as the "close" detector while detector 474 serves as the "far" detector. It should be understood that emitter 470 may include two light emitting sources in order to emit light at two wavelengths (e.g., Red and IR).

Emitter 470 and detector 472 may also be used together as a CNIBP sensor in order to measure the blood pressure of subject 402. As described above, a single CNIBP sensor may be used to measure the blood pressure of subject 402, for example, by measuring the area under one or more portions of a pulse signal detected by the CNIBP sensor. In other arrangements, a second CNIBP sensor may be disposed in a different location on subject 402 in order to calculate blood pressure using, for example, the differential pressure pulse transit time (DPTT) measurement technique described above. Proper placement of a second CNIBP sensor on subject 402, and techniques for connecting the second CNIBP sensor to sensor structure 412 or cable 404, is discussed in greater detail below in connection with FIG. 5.

Combined physiological sensor 410 may also include temperature sensor 476 for measuring the temperature of subject 402. Temperature sensor 476 may be located at any suitable position within sensor structure 412. For example, temperature sensor 476 may be positioned at a distance from emitter 470, such that heat generated by emitter 470 is not substantially included in the temperature measured by sensor 476. As another example, temperature sensor 476 may be positioned over a site of highly perfused tissue, such as directly above the eyebrow of subject 402. In the arrangement depicted in FIG. 4A, temperature sensor 476 is positioned between detectors 472 and 474. This arrangement may ensure that temperature sensor 476 is sufficiently isolated from heat generated by emitter 470, while utilizing the unused space between detectors 472 and 474—necessary for measuring regional blood oxygen saturation—advantageously. Moreover, each of these devices may be positioned together over the eyebrow in a highly perfused area.

Figure 4B:
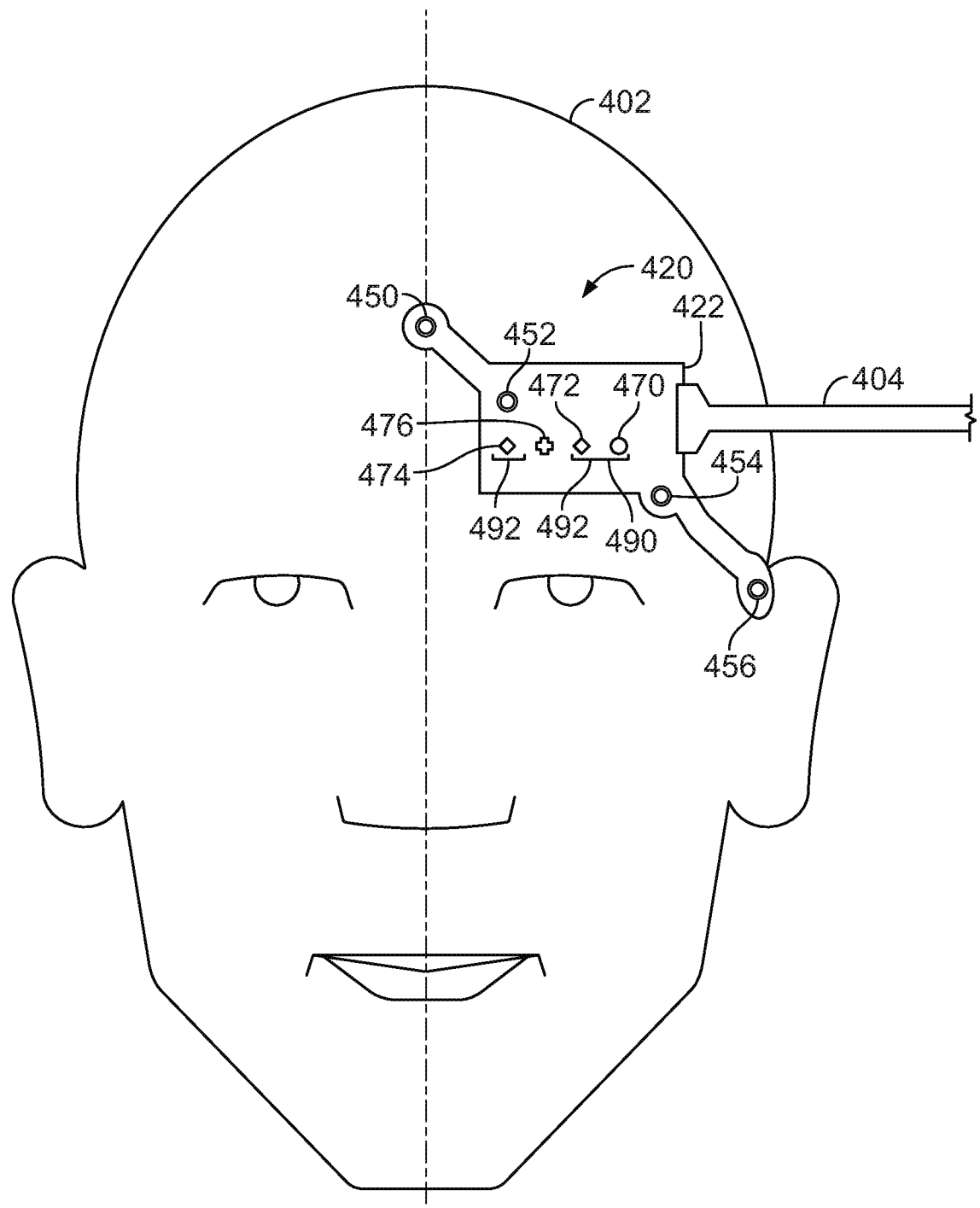
Figure 4C:
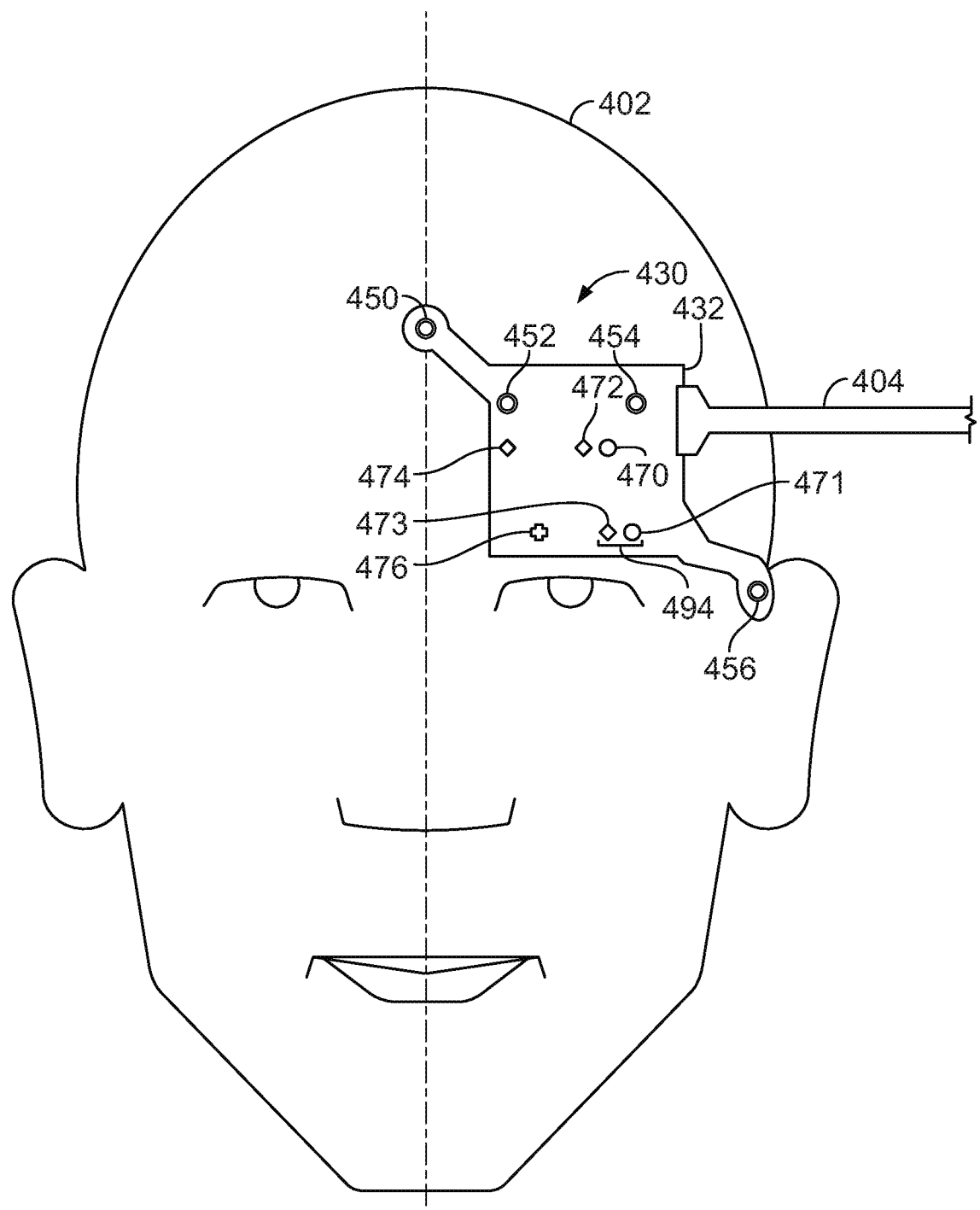
Figure 4D:
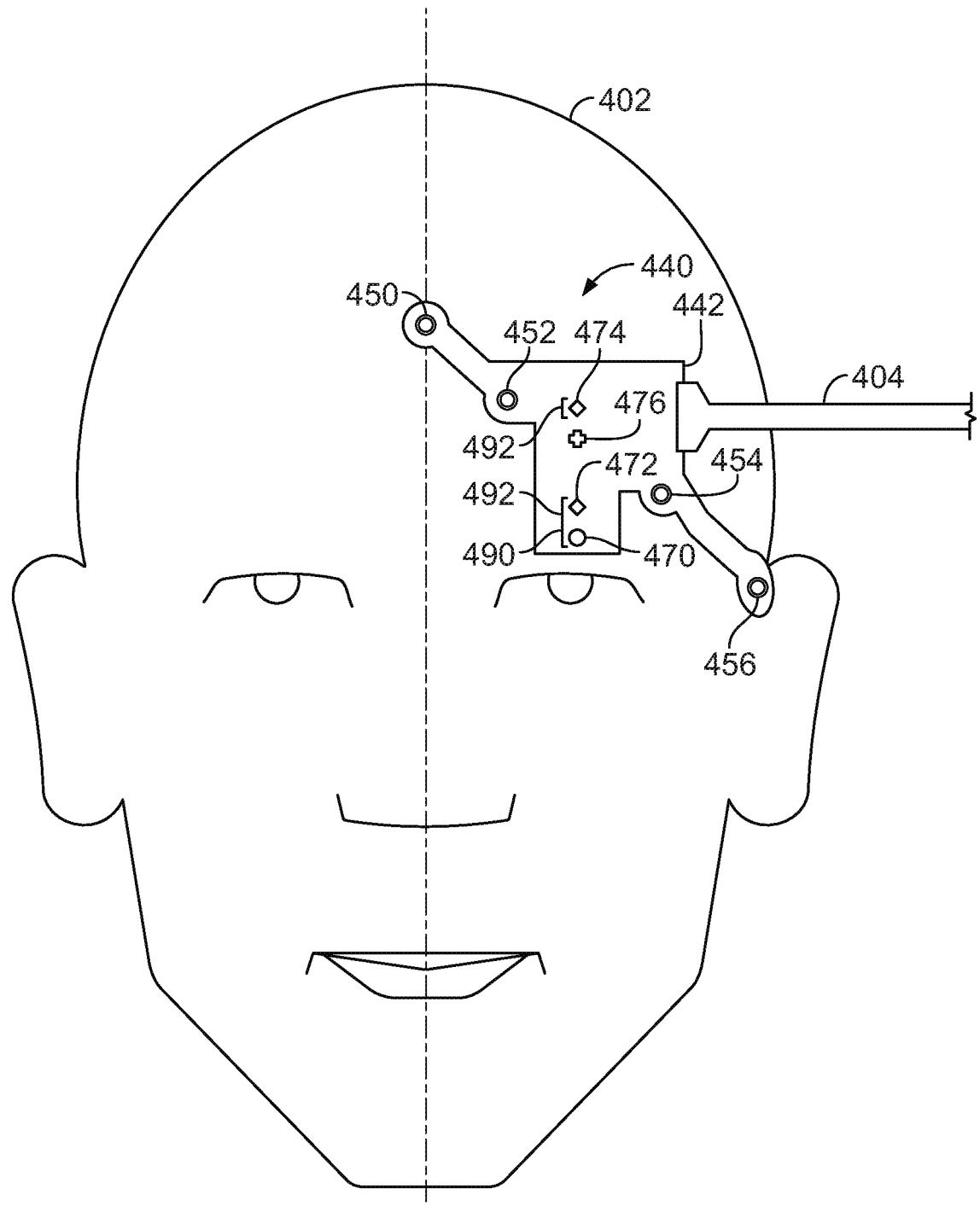

It should be understood that the locations of the sensors depicted in FIG. 4A, and the shape of sensor structure 412, are exemplary and may differ in accordance with other arrangements of the sensors, as illustrated in FIGS. 4B-4D. FIG. 4B shows an illustrative combined physiological sensor 420 attached to subject 402, in accordance with an embodiment. As shown in FIG. 4B, the locations of the various sensors incorporated into combined physiological sensor 420 differ with respect to those depicted within combined physiological sensor 410 of FIG. 4A. In particular, EEG sensor 452 is positioned to the lower right of EEG sensor 450 and EEG sensor 454 is positioned to the lower right of sensor 452. In order to accommodate the positioning of the EEG sensors in FIG. 4B, sensor structure 422 is shaped to provide an area for EEG sensor 454 below and to the right of emitter 470. In an arrangement, all or some of EEG sensors 450, 452, 454, and 456 are positioned to form a straight line and/or are equally spaced on subject 402.

FIG. 4C shows an illustrative combined physiological sensor 430 attached to subject 402, in accordance with an embodiment. In addition to, or instead of, employing emitter 470 and detector 472 as a CNIBP sensor, a separate CNIBP sensor 494 is included in sensor structure 432. CNIBP sensor 494 may include emitter 471 and detector 473, and may be positioned over tissue where pulsatility is strong over a wide variety of perfusion conditions. For example, as depicted, CNIBP sensor 494 may be positioned directly over the eyebrow of subject 402. As described above, a single CNIBP sensor (e.g., sensor 494) may be used to measure the blood pressure of subject 402, for example, by measuring the area under one or more portions of a pulse signal detected by the CNIBP sensor. As further described above, two CNIBP sensors at different locations on a subject's body may be used to estimate blood pressure by measuring the amount of time between the arrivals of corresponding points of a pulse signal at the two locations. In an arrangement, emitter 470 may be used in combination with detector 472 as one CNIBP sensor, while sensor 494 serves as the second CNIBP sensor. In another arrangement, combined physiological sensor 430 may include an additional CNIBP sensor for measuring blood pressure, as will be discussed below in connection with FIG. 5.

As further depicted in FIG. 4C, temperature sensor 476 may be advantageously positioned within sensor structure 432 at a site of high perfusion. In an arrangement, temperature sensor 476 may be positioned as close as possible to the eyebrow, subject to the limitations imposed by the area and shape of sensor structure 432. In addition, temperature sensor 476 may be disposed in an area of sensor structure 432 at a distance from any heat generating devices, such as emitters 470 and 471.

FIG. 4D shows an illustrative combined physiological sensor 440 attached to subject 402, in accordance with an embodiment. In the depicted arrangement, oximeter sensor 490 is located over an area of high perfusion and pulsatility. Moreover, sensor structure 442 is shaped to provide space for EEG sensor 454 to be positioned to the lower right of EEG sensor 452 (as in FIG. 4B). A vertical arrangement of emitter 470, detectors 472 and 474, and temperature sensor 476 is shown that allows emitter 470 and detector 472 to be disposed over highly perfused tissue. Such placement may better enable use of emitter 470 and detector 472 as a CNIBP sensor, thereby obviating the need for an additional CNIBP sensor on the subject (as in FIG. 4C). Eliminating the need for an additional CNIBP sensor reduces cost, combined physiological sensor area, and circuit complexity. The vertical arrangement of the emitter, detectors, and temperature sensor may also enable a more advantageous arrangement of the EEG sensors. For example, in an arrangement, all or some of EEG sensors 450, 452, 454, and 456 are disposed in a straight line and/or are equally spaced on subject 402.

Figure 5:
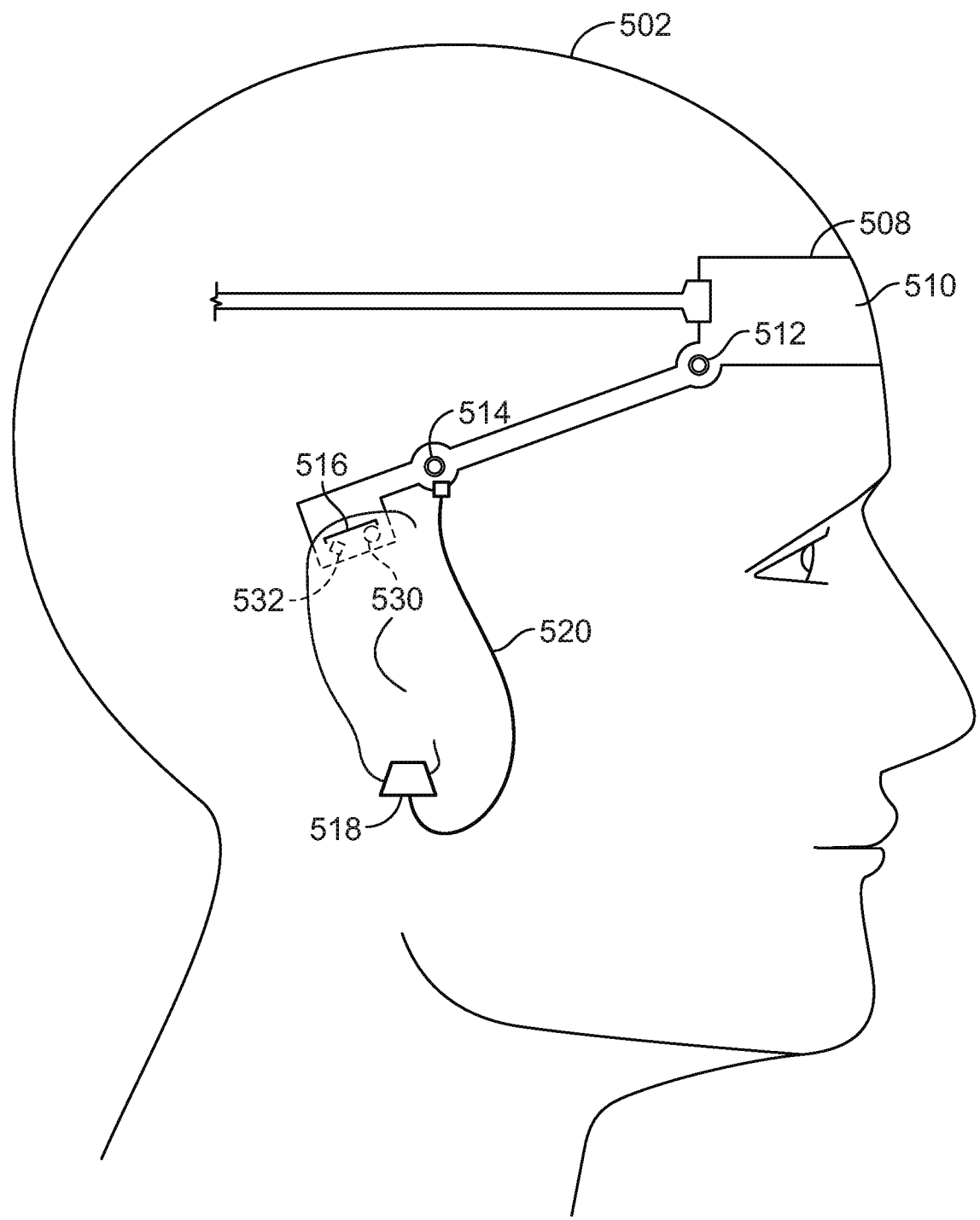
FIG. 5 shows a perspective view of a combined physiological sensor as applied to subject in accordance with an embodiment.

FIG. 5 shows a perspective view of a combined physiological sensor 508 attached to subject 502, in accordance with an embodiment. Combined physiological sensor 508 may be substantially similar to combined physiological sensor 420 of FIG. 4B or combined physiological sensor 440 of FIG. 4D. Specifically, sensor structure 510 may be substantially similar to sensor structures 422 or 442, and EEG sensors 512 and 514 may be substantially similar to, and disposed in the same location as, EEG sensors 454 and 456, respectively. In another arrangement, combined physiological sensor 508 may be substantially similar to combined physiological sensor 410 of FIG. 4A or combined physiological sensor 430 of FIG. 4C, and EEG sensor 512 may be located above the location depicted as in FIGS. 4A and 4C. Combined physiological sensor 508 may additionally include CNIBP sensors 516 or 518. Although FIG. 5 depicts both sensors 516 and 518, it should be understood that, in an embodiment, combined physiological sensor 508 may include only one of the sensors. CNIBP sensor 516 includes emitter 530 and detector 532, both of which may be incorporated into sensor structure 510 and disposed behind the ear of subject 502, as shown. CNIBP sensor 516 may be used together with another CNIBP sensor (e.g., the combination of emitter 470 and detector 472 of FIGS. 4A-4D, or CNIBP sensor 494 of FIG. 4C) to determine blood pressure using CNIBP monitoring techniques. For example, by measuring PPG signals with each CNIBP sensor, the arrival of a pulse may be detected at each sensor location. As described above, the elapsed time between the arrivals of corresponding points of a pulse signal at the two locations may be used to calculate blood pressure.

CNIBP sensor 516 may detect a PPG signal by way of receiving light, produced by emitter 530 and reflected from one or more internal substances (e.g., tissues) of subject 502, with detector 532. The received light intensity may then be used to determine a pulse signal. Although FIG. 5 shows CNIBP sensor 516 as part of sensor structure 510, it may alternatively be included in a second sensor structure and connected to sensor structure 510 through a cable or wireless device. In an embodiment, CNIBP sensor 518 may be used instead of sensor 516 for blood pressure calculation. CNIBP sensor 518 may be a clip configured to attach to or clamp down on, for example, an earlobe. The clip may include an emitter and detector on opposite sides, such that light produced by the emitter may pass through an area of tissue (e.g., through the earlobe of subject 502) and be received by the detector on the other side. The received light intensity may then be used to determine a pulse signal. CNIBP sensor 518 may be connected to sensor structure 510 via cable 520, or through wireless communication.

As described herein, CNIBP sensors are PPG sensors utilized for the purpose of measuring blood pressure. It should therefore be understood that these same PPG sensors may be utilized for any physiological measurement that relies on PPG signals, such as pulse and regional blood oxygen saturation measurement. For example, CNIBP sensors 516 and/or 518 may be used to calculate the pulse blood oxygen saturation of the subject, in addition to or instead of measuring blood pressure.

In an embodiment, each of the combined physiological sensors depicted in FIGS. 4A-4D and FIG. 5 may be applied to a subject along with a mirrored version of the respective combined physiological sensor. For example, a mirrored version of combined physiological sensor 410 of FIG. 4A (less EEG sensor 450) may be applied to subject 402 such that an EEG sensor is disposed in a location opposite that of EEG 452, symmetrical about axis 406 (the horizontal center of the forehead of subject 402). Similarly, the mirrored version of combined physiological sensor 410 may be applied such that EEG sensors are disposed opposite each of EEG sensors 454 and 456, and an emitter, two detectors, and a temperature sensor are disposed opposite emitter 470, detectors 472 and 474, and temperature sensor 476, respectively, symmetrical about axis 406. A second cable (or wireless transmitter/receiver) may connect the mirrored combined physiological sensor to a monitor, storage device, or to the non-mirrored combined physiological sensor. In an embodiment, instead of a separate mirrored combined physiological sensor, a single sensor structure may combine all the sensors into one combined physiological sensor. For example, sensor structure 412 may be expanded to incorporate duplicates of sensors 452, 454, 456, 492, and 476, each duplicate sensor disposed opposite the corresponding original sensor and symmetrically about axis 406 (e.g., an EEG sensor corresponding to EEG sensor 456 is disposed on the left temple of subject 402). In this embodiment, cable 404 may connect to both the original and duplicate sensors.

Figure 6A:
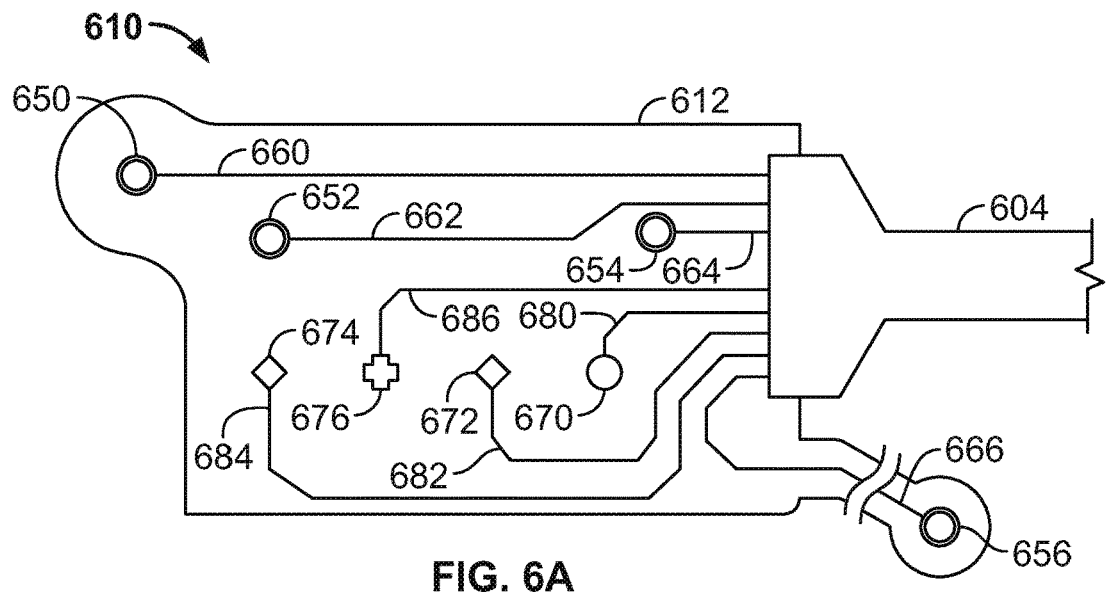
FIGS. 6A-6C show detailed views of various combined physiological sensors in accordance with some embodiments.
Figure 6B:
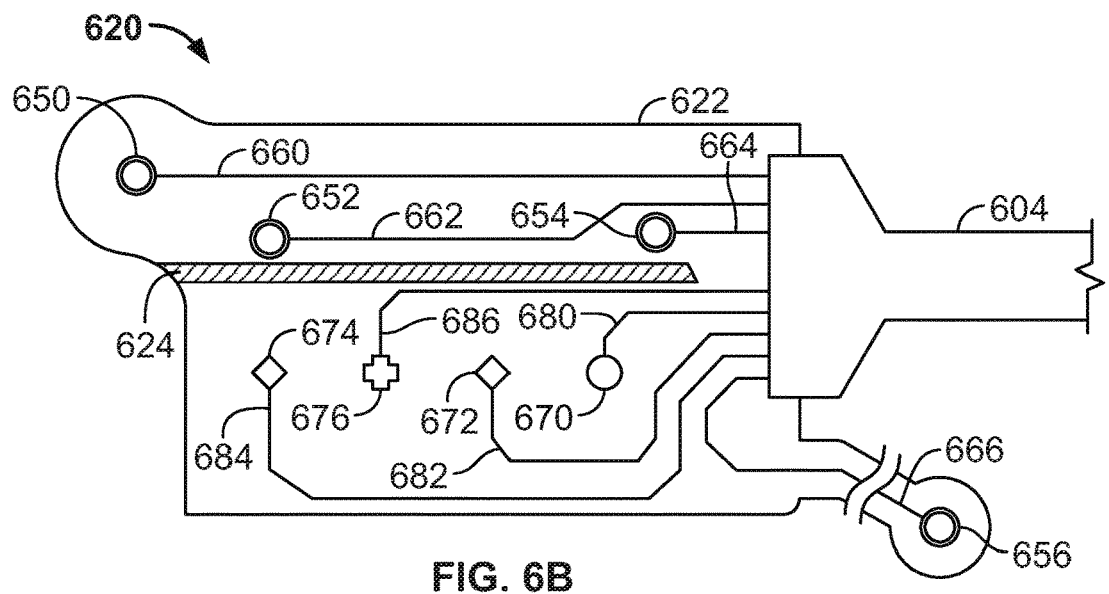
Figure 6C:
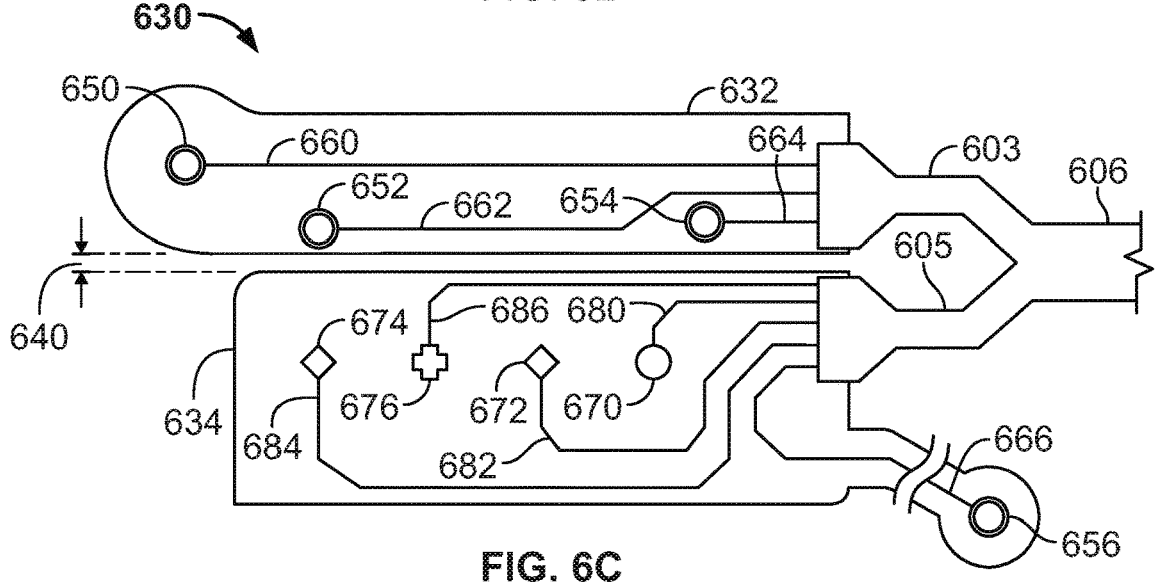

FIGS. 6A-6C show detailed views of the combined physiological sensors discussed above in connection with FIGS. 4A-4D and FIG. 5, in accordance with some embodiments. FIG. 6A shows combined physiological sensor 610 including sensor structure 612 and cable 604. Although the depiction resembles that of combined physiological sensor 410 of FIG. 4A, it should be understood that combined physiological sensor 610 may represent any of the combined physiological sensors discussed above, or any other suitable combined physiological sensor. In particular, sensor structure 612 may be substantially similar to sensor structures 412, 422, 432, or 442 of FIGS. 4A, 4B, 4C, and 4D, respectively, with corresponding disposition of the various sensors. As shown, EEG sensors 650, 652, 654, and 656 are connected to cable 604 through interconnects 660, 662, 664, and 666, respectively. Interconnects 660, 662, 664, and 666 may be wires, metallic traces, or other conductive material, and may be deposited on, or embedded within, sensor structure 612. Furthermore, emitter 670, detectors 672 and 674, and temperature sensor 676 are connected to cable 604 through interconnects 680, 682, 684, and 686, respectively. Interconnects 680, 682, 684, and 686 may be wires, metallic traces, or other conductive material, and may be deposited on, or embedded within, sensor structure 612. Although shown as single lines, each of interconnects 680, 682, 684, and 686 may include two or more distinct interconnects, as required by the corresponding sensor. For example, emitter 670, detectors 672 and 674, and/or temperature sensor 676 may be two-node devices requiring two wires, traces, or other conductive material in order for the sensors to function properly. In an embodiment, sensors connected in the "series" circuit topology may be connected to cable 604 through two interconnects carrying the same current, and sensors connected in the "parallel" circuit topology may be connected to cable 604 through two interconnects over which a voltage may be measured, one of which may be electrical (or earth) ground.

In an embodiment, emitter 670 and detectors 672 and 674 may be located remotely from combined physiological sensor 610 (e.g., at monitor 14 of FIG. 1) and interconnects 680, 682, and/or 684 may be fiberoptic lines (or cables), suitable to carry light to and from combined physiological sensor 610. For example, light emitted by a remotely located emitter 670 may be transmitted through a fiberoptic channel within cable 604 to fiberoptic line 680, through which the light may travel to an aperture that directs the light into a subject. Reflected light may, in turn, be received with fiberoptic lines 682 and 684 and the light may be transmitted through one or more fiberoptic channels within cable 604 to remotely located detectors 672 and 674, respectively. The use of fiberoptics with PPG sensors is described in greater detail in U.S. patent application Ser. No. 12/944,950, "SYSTEMS AND METHODS FOR COMBINED PHYSIOLOGICAL SENSORS," filed Nov. 12, 2010, which is hereby incorporated by reference herein in its entirety.

As depicted in FIG. 6A, the various interconnects may be disposed in a manner that reduces crosstalk or interference between the sensors. For example, interconnects associated with some or all of the EEG sensors may be disposed at a distance from the interconnects associated with the PPG sensors. In an arrangement, an interconnect associated with a temperature sensor may be located between the interconnects associated with the EEG sensors and the interconnects associated with the PPG sensors. In another arrangement, a ground line (e.g., wire or metallic trace) may be run between, and thus divide, the aforementioned interconnects. In the arrangement shown in FIG. 6A, interconnects 660, 662, and 664 are disposed in the upper area of sensor structure 612, while interconnects 680, 682, and 684 are disposed in the lower area of sensor structure 612. Interconnect 686 is disposed in the center of sensor structure 612 and separates interconnects 660, 662, and 664 from interconnects 680, 682, and 684. Interconnect 666 is disposed at the bottom of sensor structure 612 and is arranged such that a minimum amount of the interconnect is in proximity of interconnect 684. Although not shown, ground plates, lines, or traces may be located anywhere on or within sensor structure 612, such as between any two interconnects, to help mitigate crosstalk and interference.

FIG. 6B shows combined physiological sensor 620 including sensor structure 622 and cable 604. The shape of sensor structure 622 may be substantially similar to sensor structure 612 of FIG. 6A, with substantially the same arrangement of sensors. In order to further isolate the EEG sensor signals from the PPG sensor signals, conductive or nonconductive flex circuit material may be removed from sensor structure 622 such that structure area 624 is revealed. Area 624 may be left exposed, such that an internal layer of sensor structure 622 is revealed. For example, the top of a foam layer on the underside of sensor structure 622 may be exposed. Alternatively, in an embodiment, area 624 may be filled with electrically conductive, non-conductive, or isolating material. For example, area 624 may be filled with a conductive material connected to electrical ground (e.g., via a ground wire provided within cable 604). As shown, area 624 is positioned between the EEG interconnects (i.e., interconnects 660, 662, and 664) and the PPG sensor and temperature sensor interconnects (i.e., interconnects 680, 682, 684, and 686). It should be understood, however, that area 624 may be located in any suitable location for reducing noise and crosstalk between sensor signals, and that multiple areas with removed flex circuit material may be present on sensor structure 622. For example, flex circuit material may be removed in the area between interconnects 684 and 666 in order to isolate the signal associated with detector 674 from the signal associated with EEG sensor 656. Moreover, it should be understood that area 624, and other similar areas, may be of any suitable shape and size. For instance, as depicted in FIG. 6B, area 624 may not extend all the way to cable 604, thus ensuring continuity of the flex circuit material of sensor structure 622. Any area of sensor structure 612 not stripped of flex circuit material may be used for routing conductive traces or wires (or fiber optic lines), or to mount devices. For example, a cable connector for linking cable 604 to the sensors and interconnects of the combined physiological sensor may be embedded within or mounted on an area of the sensor structure (e.g., structure 622) that contains flex circuit material.

As discussed above, area 624 may be formed by scraping, cutting, or otherwise removing flex circuit material from sensor structure 622. Alternatively, flex circuit material may have never been placed or deposited in the location of area 624. For example, flex circuit material of the shape shown in FIG. 6B (i.e., the shape of sensor structure 622 less area 624) may have been fabricated initially. It should be understood that any suitable technique for removing or preventing flex circuit material from disposition in area 624 may be used in accordance with the present disclosure.

FIG. 6C shows combined physiological sensor 630 including sensor structures 632 and 634, as well as Y-cable 606. In the depicted embodiment, EEG sensors 650, 652, and 654 are incorporated into sensor structure 632, while emitter 670, detectors 672 and 674, and temperature sensor 676 are incorporated into sensor structure 634. The use of two sensor structures may enable a high degree of isolation between the EEG sensor signals on the one hand, and the PPG and temperature sensor signals on the other. In addition, the level of isolation may be increased or decreased by varying the gap 640 between sensor structures 632 and 634. As shown, Y-cable 606 may include cable heads 603 and 605 for connection to the sensors of sensor structures 632 and 634, respectively. In particular, cable head 603 may receive signals from EEG sensors 650, 652, and 654 through interconnects 660, 662, and 664, respectively, Cable head 605 may receive signals from emitter 670, detectors 672 and 674, and temperature sensor 676 through interconnects 680, 682, 684, and 686, respectively. In addition to enhanced isolation, the use of multiple sensor structures further allows targeted placement of the sensors on a subject. For example, the EEG sensors on sensor structure 632 may be placed in the most suitable location for EEG signal measurement (e.g., centered on a subject's forehead), while the PPG sensors on sensor structure 634 may be placed in the most suitable location for oxygen saturation or blood pressure measurement (e.g., above the eyebrow on subject's forehead, in an area of high pulsatility). EEG sensor 656 and interconnect 666 may be incorporated into sensor structure 634 and connected to cable head 605, as shown. It should be understood, however, that in other arrangements, sensor 656 and element 666 may be incorporated into sensor structure 632 and connected to cable head 603, or they may be incorporated into a third sensor structure connected directly to cable 606 (e.g., through a third cable head).

Figure 7A:
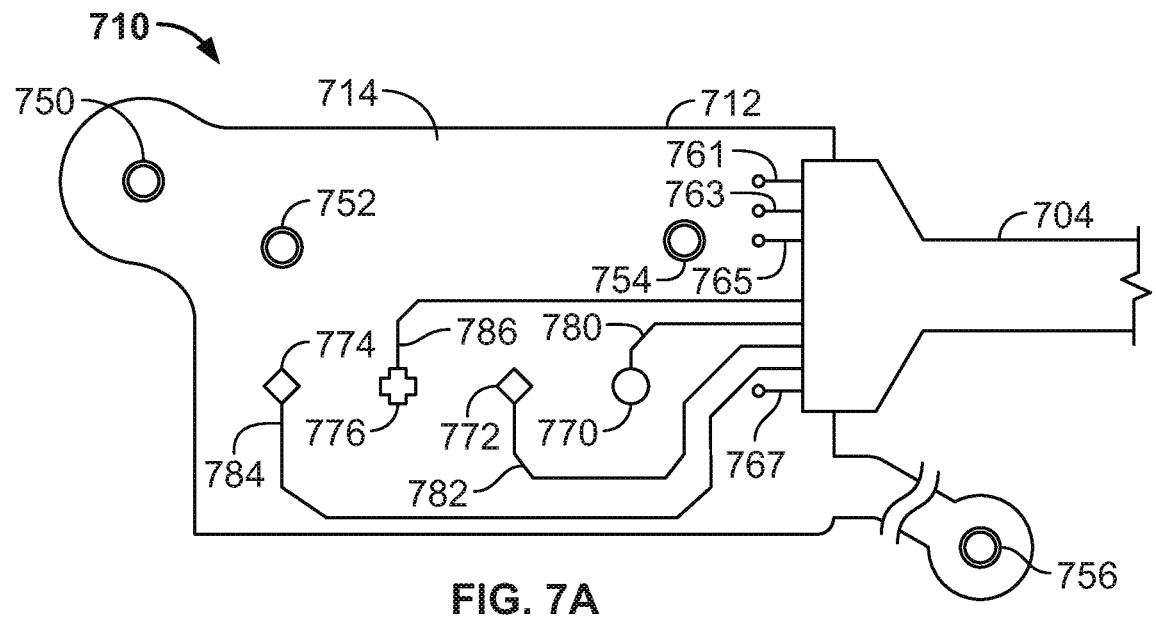
FIGS. 7A and 7B show top and bottom views, respectively, of a combined physiological sensor in accordance with an embodiment.
Figure 7B:
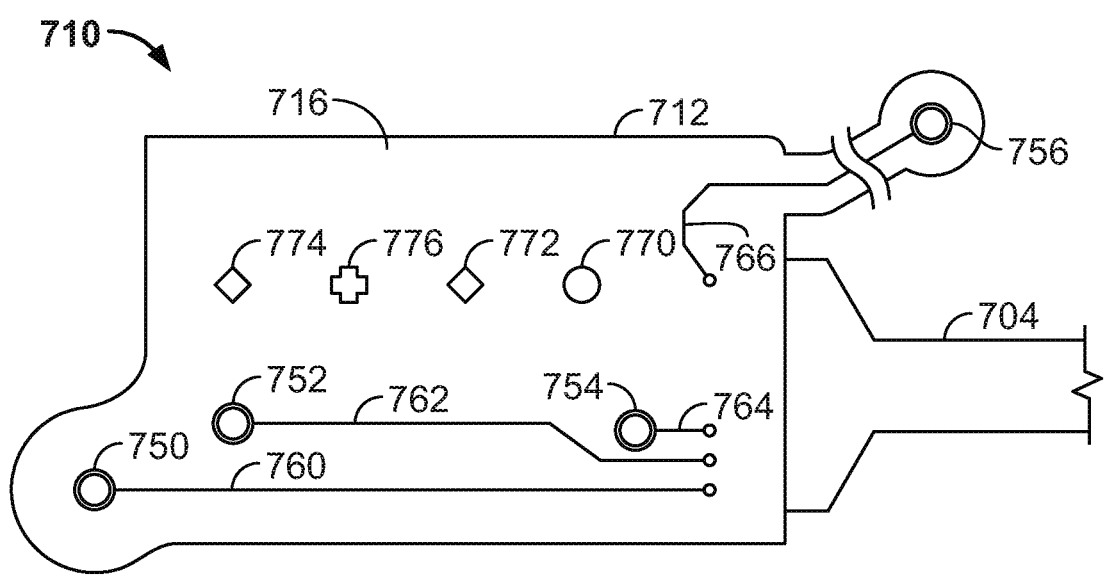

FIGS. 7A and 7B show top and bottom views, respectively, of a combined physiological sensor 710 in accordance with an embodiment. Although combined physiological sensor 710, as depicted, resembles that of combined physiological sensor 410 of FIG. 4A, it should be understood that combined physiological sensor 710 may represent any of the combined physiological sensors discussed above (e.g., in connection with FIGS. 4A-4D and FIG. 5), or any other suitable combined physiological sensor. In particular, sensor structure 712 may be substantially similar to sensor structures 412, 422, 432, or 442 of FIGS. 4A, 4B, 4C, and 4D, respectively, with corresponding disposition of the various sensors. FIG. 7A shows top surface 714 of sensor structure 712 included within combined physiological sensor 710. EEG sensors 750, 752, 754, and 756, emitter 770, detectors 772 and 774, and temperature sensor 776 may be embedded within or mounted on sensor structure 712. In an embodiment, a portion of EEG sensors 750, 752, 754, and 756 may be exposed and/or accessible both at top surface 714 of FIG. 7A and at bottom surface 716 of FIG. 7B. For example, the tops of the EEG sensors may be substantially flush with (or may slight protrude from) top surface 714 and/or the bottoms of the EEG sensors may be substantially flush with (or may slight protrude from) bottom surface 716. In another embodiment, the EEG sensors may be exposed and/or accessible only at bottom surface 716 of FIG. 7B, in which case the depictions of the EEG sensors in FIG. 7A simply indicate the locations of the EEG sensors embedded within sensor structure 712 or mounted on bottom surface 716 of FIG. 7B. Emitter 770, detectors 772 and 774, and temperature sensor 776 may be connected to cable 704 through interconnects 780, 782, 784, and 786, respectively. Interconnects 780, 782, 784 and 786 may be wires, metallic traces, or other conductive material, and may be deposited on, or embedded within, top surface 714 of sensor structure 712. Although shown as single lines, each of interconnects 780, 782, 784, and 786 may include two or more distinct interconnects, as required by the corresponding sensors, one of which may be connected to electrical (or earth) ground (e.g., via a ground wire provided within cable 704). Alternatively, as discussed above, interconnects to the PPG sensors (e.g., interconnects 780, 782, and 784) may be fiber optic lines configured to transfer light between combined physiological sensor 710 and remotely located emitters and detectors (e.g., remotely located emitter 770 and detectors 772 and 774).

FIG. 7B shows bottom surface 716 of sensor structure 712 included within combined physiological sensor 710. EEG sensors 750, 752, 754, and 756 may be connected to cable 704 through interconnects 760, 762, 764, and 766 of FIG. 7B—which may deposited on, or embedded within, bottom surface 716—and interconnects 761, 763, 765, and 767 of FIG. 7A—which may be deposited on, or embedded within, top surface 714. Specifically, interconnects 760, 762, 764, and 766 may be connected, through structure 712, to interconnects 761, 763, 765, and 767, respectively, such that each pair of interconnects forms a single conductive line between an EEG sensor and cable 704. In this arrangement, interconnects 760, 762, 764, and 766 can be separated from interconnects 780, 782, 784, and 786, thus preventing a measure of cross-talk between the PPG and temperature sensor signals carried via the interconnects on top surface 714 and the EEG signals carried via the interconnects on bottom surface 716. As depicted, interconnects 761, 763, 765, and 767 on top surface 714 enable interconnects 760, 762, 764, and 766 on bottom surface 716 to access cable 704, which may connect to sensor structure 712 by way of a cable connector mounted on top surface 714. Interconnects 761, 763, 765, and 767 may be wires, metallic traces, or other conductive material, and may be deposited on, or embedded within, top surface 714 of sensor structure 712. Interconnects 760, 762, 764, and 766 may be wires, metallic traces, or other conductive material, and may be deposited on, or embedded within, bottom surface 716 of sensor structure 712.

As described above, disposing the interconnects associated with the EEG sensors and the interconnects associated with the PPG and temperature sensors on opposite sides of sensor structure 712 may facilitate the reduction of noise and cross-talk affecting the sensor signals. In addition, sensor structure 712 may include an intervening layer—between top surface 714 and bottom surface 716—to further reduce interference between the two sets of signals. For example, the intervening layer may be a non-conductive or dielectric material, or the intervening layer may be connected to electrical ground (e.g., via a ground wire provided within cable 704).

Furthermore, the length of interconnects 761, 763, 765, and 767 may be minimized to reduce the amount of conductive material associated with the EEG sensors located on top surface 714. It should be understood that the techniques illustrated in FIGS. 6A-6C and FIG. 7 are not exclusive, but intended to describe methods of reducing noise, interference, cross-talk, or other signal corruptions that occur as a result of proximity between the various sensors and interconnects. As such, modifications to the positioning of the individual sensors, interconnects, and the combined physiological sensor structure that further accomplish noise reduction are within the scope of this disclosure. For example, referring to FIG. 7A, interconnects 761, 763, 765, and 767 need not be disposed lengthwise on top surface 714, but may travel upwards from bottom surface 716 towards surface 714, up directly beneath cable 704 (or a cable connector for attaching cable 704). Alternatively, interconnects 761, 763, 765, and 767 may not be present and interconnects 760, 762, 764, and 766 may connect directly to cable 704 (or a cable connector for attaching cable 704) on bottom surface 716.

Figure 8:
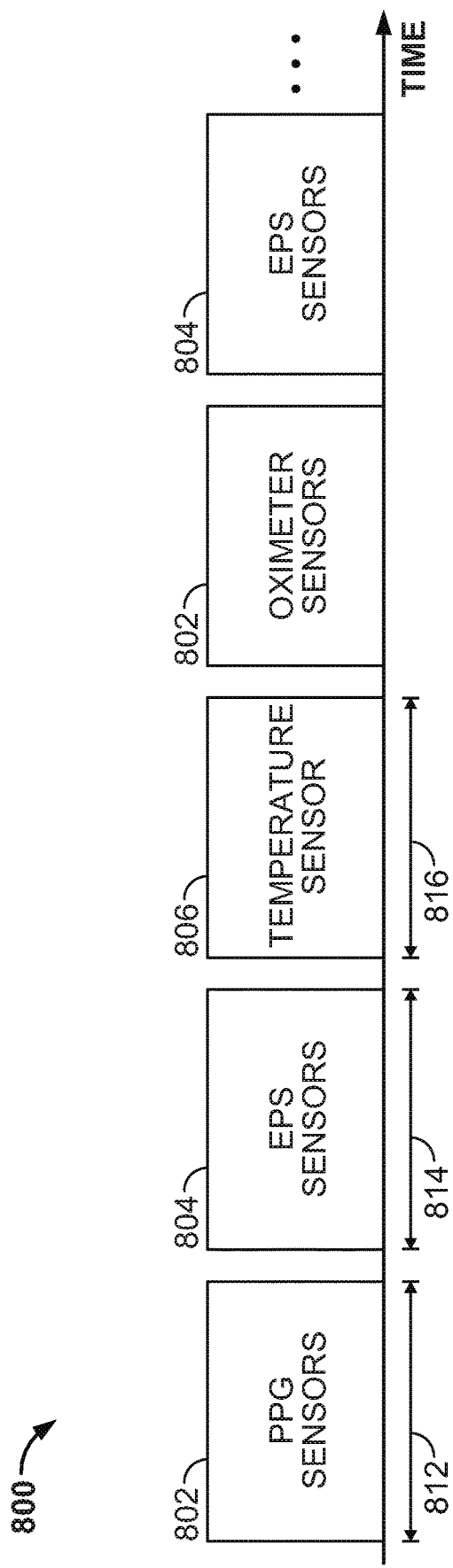
FIG. 8 is an illustrative timing diagram for activating the assorted sensors of a combined physiological sensor in accordance with an embodiment.

FIG. 8 shows an illustrative timing diagram 800 for activating the various sensors of a combined physiological sensor, in accordance with an embodiment. In particular, timing diagram 800 shows a repeating pattern of three time intervals, wherein a different sensor set is active during each of the time intervals. For example, in first time interval 812, PPG sensors 802 may be active, including pulse and regional oxygen saturation sensors and/or CNIBP sensors. The sensors may include emitters and detectors, such as emitter 770 and detectors 772 and 774 of FIG. 7. In second time interval 814, EPS sensors 804 may be active, including EEG sensors such as sensors 750, 752, 754, and 756 of FIG. 7. In third time interval 816, temperature sensor 806 may be active, such as sensor 776 of FIG. 7. Although each of time intervals 812, 814, and 816 are shown having the same duration, it should be understood that the duration of each may vary as suitable for each particular set of sensors to successfully obtain and/or transmit signal measurements. Specifically, the duration of each time interval may be the time required for the particular sensors in the corresponding sensor set to accurately process a measurement and/or to transmit a signal. For example, the duration of time interval 812 may be the time required for a PPG signal to be measured by PPG sensors 802 and/or transmitted to a data collection or transmission device, such as a memory chip, cable, or patient monitor. In addition, although timing diagram 800 includes a period of time between each time interval, in another embodiment, each time interval may immediately follow the previous time interval or two or more time intervals may overlap (e.g., partly or completely).

It should be understood that the durations, spacing or overlap, and order of time intervals 812, 814, and 816 in timing diagram 800 may be configured in any manner that reduces, prevents, or limits interference between signals generated by PPG sensors 802, EPS sensors 804, and temperature sensors 806. For example, time interval 816 may occur before time interval 814. As another example, time interval 816 may span virtually the entire time axis (i.e., temperature sensor 806 may be active at all times), while time intervals 812 and 814 alternate continuously. It should also be understood that additional time intervals may be included during which sensors 802, 804, 806, other sensors, or a combination thereof are active. For example, PPG sensors 802 may be active both during time interval 812 and in another time interval occurring between time intervals 814 and 816. As another example, one (or more) of PPG sensors 802 may be active during time interval 812 while another one (or more) of PPG sensors 802 may be active in another time interval (e.g., subsequent to time interval 802 but before time interval 814).

Activation of sensors 802, 804, and 806 may be controlled by a patient monitor or other sensor control device (e.g., within the combined physiological sensor). For example, as discussed above, TPU 58, within monitor 14, of FIG. 2 may be connected directly, or through other control circuitry, to each of the sensors of the combined physiological sensor. In such an arrangement, TPU 58 may control the timing and duration of each sensor's activity. Specifically, TPU 58 may enable and disable sensors 802, 804, and 806 in accordance with timing diagram 800 of FIG. 8. In an embodiment, a sensor control device attached to, or embedded within, the combined physiological sensor may enable and disable sensors 802, 804, and 806 in accordance with timing diagram 800 of FIG. 8. For example, combined physiological sensor 710 of FIGS. 7A and 7B may contain a sensor control device connected between the connection paths (e.g., paths 761-767 and 780-786) and cable 704. As another example, cable 704 may itself contain a sensor control device that activates or deactivates each of the connection paths connected to the cable. As yet another example, a sensor control device may reside between a cable (or wireless receiver) and a patient monitor to which the cable (or wireless receiver) is connected. In an embodiment, both a patient monitor and sensor control device may be used to control sensors 802, 804, and 806 in accordance with timing diagram 800 of FIG. 8. For example, a patient monitor may issue requests for various measurements from the sensors (in sequence or in parallel), and a sensor control device may receive, process, and/or store the requests and may activate and deactivate the sensors in accordance with timing diagram 800. In one case, for instance, a patient monitor may request PPG and EPS measurements in one instant and a temperature measurement the next instant. The sensor control device may receive these requests and activate the corresponding sensors in the proper sequence and with the proper spacing/overlap and duration, as determined by timing diagram 800.

Timing diagram 800 of FIG. 8, and in particular the order, spacing, and durations of time intervals 812, 814, and 816, may be predetermined and stored as data or executable instructions in memory (e.g., in memory 322 of FIG. 3), which may be accessed by processing circuitry (e.g., TPU 58 of FIG. 2 or processor 312 of FIG. 3) to properly time the activation of the sensors. Alternatively, the order, spacing, and durations of time intervals 812, 814, and 816 may be implemented directly as part of the processing circuitry (e.g., TPU 58 or a sensor control device). In an embodiment, timing diagram 800, and in particular the order, spacing, and/or durations of time intervals 812, 814, and 816, are not predetermined. In one approach, each time interval may continue until one or more of the corresponding sensors successfully detects, measures, and/or processes a signal, or until one or more of the corresponding sensors produces a sensor output signal and/or transmits the output signal to a storage or other transmission device. For example, time interval 812 may be initiated (i.e., PPG sensors 802 may be activated) and may continue until a signal is successfully detected, measured, processed, and/or a sensor output signal is transmitted by PPG sensors 802. In some cases, there may be a maximum limit to the duration of a time interval so that all sets of sensors may eventually operate even if one or more sets of sensors fail to detect or measure a signal. For example, if PPG sensors 802 fail to measure a PPG signal within a certain amount of time (predetermined or calculated on the fly) of the onset of time interval 812, time interval 812 may end and time interval 814 may begin. In other cases, a time interval may be cut short by the initiation of another time interval. For example, time interval 814 may be configured to continuously occur at a defined frequency and time intervals 812 and 814 may continue (if necessary) until the onset of time interval 814. As another example, a patient or other operator may manually request a reading from one of the sensor sets and, upon reception of the request, any active sensors not within the requested sensor set may be disabled and the requested sensor set may be enabled. In other words, upon reception of a manual request, all time intervals may be ended immediately and the time interval corresponding to the requested sensor set may begin. For instance, when an operator requests an SpO₂ measurement during time interval 814 or 816, the current time interval may end and time interval 812 may begin.

The terms activation/deactivation or enablement/disablement of sensors, as used herein, should be understood to mean any of providing/severing power to a sensor, providing/severing a data signal to a sensor, and/or allowing/disallowing capture or analysis of a sensor output signal. In addition, it should be understood that while the description above referred to enabling/disabling all sensors in a sensor set (e.g., all PPG sensors 802 or all EPS sensors 804), less than all the sensors in a sensor set may be accordingly enabled/disabled. For example, EEG sensor 756 of FIG. 7 may remain active even when EEG sensors 750, 752, and 754 are deactivated (e.g., insofar as EEG sensor 756 may not interfere with any of the PPG or temperature sensors, even when active). Lastly, it should be understood that sensor activation/deactivation may be controlled by any suitable system or apparatus configured to execute machine-readable (or computer-readable) instructions stored on a machine-readable (or computer-readable) medium.

The foregoing is merely illustrative of the principles of this disclosure and various modifications may be made by those skilled in the art without departing from the scope and spirit of the disclosure. The following claims may also describe various aspects of this disclosure.

What is claimed is:

1. A multi-sensor monitoring system comprising:
a substrate comprising a surface;
a plurality of sensors disposed on the surface of the substrate such that an outer perimeter of the substrate surrounds each sensor of the plurality of sensors, wherein the plurality of sensors comprises at least two of: a photoplethysmographic (PPG) sensor, an electrical physiological signal (EPS) sensor, or a temperature sensor, wherein the at least two sensors of the plurality of sensors are different from one another; and
sensor control circuitry of a patient monitor configured to:
activate and deactivate a first sensor of the plurality of sensors in accordance with a timing scheme, wherein the patient monitor determines a first physiological parameter based on signals received from the first sensor;
activate and deactivate a second sensor of the plurality of sensors in accordance with the timing scheme, the first and second sensors being different types of sensors, wherein the patient monitor determines a second physiological parameter based on signals received from the second sensor;
adjust the timing scheme based on the determined first physiological parameter from the first sensor or the determined second physiological parameter from the second sensor; and
wherein the timing scheme comprises at least one first sensor activation time period during which the first sensor is active and wherein the second sensor is inactive during the at least one first sensor activation time period.

2. The multi-sensor monitoring system of claim 1, wherein the patient monitor is coupled to the plurality of sensors, and wherein the patient monitor is configured to:
receive signals from the first sensor and the second sensor;
determine the first physiological parameter and the second physiological parameter of a subject based on the received signals; and display the first physiological parameter, the second physiological parameter, or a combination thereof, using a display.

3. The multi-sensor monitoring system of claim 2, wherein the sensor control circuitry is configured to adjust the timing scheme based on a user input.

4. The multi-sensor monitoring system of claim 2, wherein the first physiological parameter is at least one of: oxygen saturation, pulse rate, temperature, blood pressure, respiration rate, or depth of consciousness.

5. The multi-sensor monitoring system of claim 1, wherein each sensor of the plurality of sensors is a part of a combined physiological sensor structure.

6. The multi-sensor monitoring system of claim 1, wherein the sensor control circuitry is a component of a sensor control device that is coupled to the plurality of sensors and to the patient monitor.

7. The multi-sensor monitoring system of claim 1, wherein the first sensor is the PPG sensor and wherein the second sensor is one of the EPS sensor or the temperature sensor.

8. The multi-sensor monitoring system of claim 1, wherein the timing scheme comprises at least one second sensor activation time period during which the second sensor is active, wherein the first sensor is inactive during the at least one second sensor activation time period, and wherein the timing scheme further comprises at least one time period between the at least one first sensor activation time period and the at least one second sensor activation time period during which both the first sensor and the second sensor are inactive.

9. The multi-sensor monitoring system of claim 1, wherein a duration of the at least one first sensor activation time period is based on a time to determine the first physiological parameter based on the signals received from the first sensor or the second physiological parameter based on the signals received from the second sensor.

10. The multi-sensor monitoring system of claim 9, wherein sensor control circuitry is configured to adjust the duration of the at least one first sensor activation time period to lengthen the activation of the first sensor until the first physiological parameter is determined based on the signals received from the first sensor.

11. The multi-sensor monitoring system of claim 9, wherein sensor control circuitry is configured to adjust the duration of the at least one first sensor activation time period to lengthen the activation of the second sensor until the second physiological parameter is determined based on the signals received from the second sensor.

12. The multi-sensor monitoring system of claim 4, wherein the second physiological parameter is a different one of oxygen saturation, pulse rate, temperature, blood pressure, respiration rate, or depth of consciousness than the first physiological parameter.

13. A method for operating a multi-sensor subject monitoring system, the method comprising:
activating and deactivating, using sensor control circuitry of a patient monitor, a first sensor of a plurality of sensors of the multi-sensor subject monitoring system in accordance with a timing scheme, wherein the patient monitor determines a first physiological parameter based on signals received from the first sensor;
activating and deactivating, using the sensor control circuitry, a second sensor of the plurality of sensors of the multi-sensor subject monitoring system in accordance with the timing scheme, the first and second sensors being different types of sensors, wherein the patient monitor determines a second physiological parameter based on signals received from the second sensor, wherein the first sensor and the second sensor are disposed on a surface of a sensor structure having an outer perimeter that surrounds both the first sensor and the second sensor; and
adjusting, using the sensor control circuitry, the timing scheme based on the determined first physiological parameter from the first sensor or the determined second physiological parameter from the second sensor,
wherein the plurality of sensors of the multi-sensor subject monitoring device comprises at least two of: a photoplethysmographic (PPG) sensor, an electrical physiological signal (EPS) sensor, or a temperature sensor,
and
wherein the timing scheme comprises at least one first sensor activation time period during which the first sensor is active and wherein the second sensor is inactive during the at least one first sensor activation time period.

14. The method of claim 13, further comprising:
receiving, using the patient monitor, signals from the plurality of sensors, wherein the patient monitor comprises the sensor control circuitry;
determining, using the patient monitor, the first physiological parameter and the second physiological parameter of the subject based on the received signals; and
displaying, using a display, the first physiological parameter, the second physiological parameter, or a combination thereof.

15. The method of claim 14, further comprising:
adjusting the timing scheme based on a user input.

16. The method of claim 14, wherein the first physiological parameter is at least one of: oxygen saturation, pulse rate, temperature, blood pressure, respiration rate, or depth of consciousness, and the second physiological parameter is a different one of oxygen saturation, pulse rate, temperature, blood pressure, respiration rate, or depth of consciousness than the first physiological parameter.

17. The method of claim 13, wherein each sensor of the plurality of sensors is a part of a combined physiological sensor structure.

18. The method of claim 13, wherein the sensor control circuitry is communicatively coupled to the plurality of sensors and to the patient monitor.

19. The method of claim 13, wherein the first sensor is the PPG sensor, and the second sensor is one of the EPS sensor or the temperature sensor.

20. The method of claim 13, wherein the timing scheme comprises at least one second sensor activation time period during which the second sensor is active, wherein the first sensor is inactive during the at least one second sensor activation time period, and wherein the timing scheme further comprises at least one time period between the at least one first sensor activation time period and the at least one second sensor activation time period during which both the first sensor and the second sensor are inactive.

* * * * *